United States Patent
Park et al.

(10) Patent No.: US 10,052,393 B2
(45) Date of Patent: Aug. 21, 2018

(54) MULTIFUNCTIONAL NANOMATERIALS FOR THE TREATMENT OF CANCER

(71) Applicant: THE REGENTS OF THE UNIVERSITY OF COLORADO, A BODY CORPORATE, Denver, CO (US)

(72) Inventors: Wounjhang Park, Superior, CO (US); Thomas Flaig, Englewood, CO (US); Xiaoping Yang, Englewood, CO (US); Lih-Jen Shih Su, Denver, CO (US); Kazunori Emoto, Broomfield, CO (US)

(73) Assignee: THE REGENTS OF THE UNIVERSITY OF COLORADO, A BODY CORPORATE, Denver, CO (US)

(*) Notice: Subject to any disclaimer, the term of this patent is extended or adjusted under 35 U.S.C. 154(b) by 770 days.

(21) Appl. No.: 14/374,588

(22) PCT Filed: Jan. 25, 2013

(86) PCT No.: PCT/US2013/023174
§ 371 (c)(1),
(2) Date: Jul. 25, 2014

(87) PCT Pub. No.: WO2013/112856
PCT Pub. Date: Aug. 1, 2013

(65) Prior Publication Data
US 2014/0378831 A1 Dec. 25, 2014

Related U.S. Application Data

(60) Provisional application No. 61/591,197, filed on Jan. 26, 2012.

(51) Int. Cl.
*A61K 9/00* (2006.01)
*A61K 49/00* (2006.01)
(Continued)

(52) U.S. Cl.
CPC ........ *A61K 49/0019* (2013.01); *A61B 5/0071* (2013.01); *A61B 18/04* (2013.01);
(Continued)

(58) Field of Classification Search
CPC .................................................. A61K 49/0019
See application file for complete search history.

(56) References Cited

U.S. PATENT DOCUMENTS

2011/0263920 A1   10/2011   Bourke et al.

FOREIGN PATENT DOCUMENTS

WO        2010107720 A2      9/2010

OTHER PUBLICATIONS

Written Opinion of the International Searching Authority and International Search Report in International Application PCT/US2013/023174 dated Jun. 27, 2013.
(Continued)

*Primary Examiner* — Paul W Dickinson
(74) *Attorney, Agent, or Firm* — Nevrivy Patent Law Group P.L.L.C.

(57) ABSTRACT

The invention relates to a multifunctional nanomaterial comprising a nanorod comprising 1) a noble metal, wherein the nanorod exhibits surface plasmon resonance absorption in the near-infrared spectrum; 2) an up-conversion phosphor that absorbs infrared light and emits visible luminescence; and optionally 3) a biomolecule targeting moiety. The invention further relates to methods of detecting and treating cancer using the multifunctional nanomaterials of the invention.

12 Claims, 15 Drawing Sheets

(51) Int. Cl.

| | |
|---|---|
| C07K 16/28 | (2006.01) |
| A61K 41/00 | (2006.01) |
| B22F 1/00 | (2006.01) |
| B82Y 30/00 | (2011.01) |
| C09K 11/77 | (2006.01) |
| A61B 5/00 | (2006.01) |
| A61B 18/04 | (2006.01) |
| A61K 33/24 | (2006.01) |
| A61N 5/06 | (2006.01) |
| A61K 47/68 | (2017.01) |
| A61K 47/69 | (2017.01) |
| B82Y 5/00 | (2011.01) |
| A61B 18/00 | (2006.01) |

(52) U.S. Cl.
CPC .......... *A61K 33/24* (2013.01); *A61K 41/0052* (2013.01); *A61K 47/6849* (2017.08); *A61K 47/6923* (2017.08); *A61N 5/062* (2013.01); *B22F 1/0025* (2013.01); *B82Y 30/00* (2013.01); *C07K 16/2863* (2013.01); *C09K 11/7772* (2013.01); *C09K 11/7777* (2013.01); *A61B 2018/00577* (2013.01); *A61N 2005/0659* (2013.01); *B82Y 5/00* (2013.01)

(56) References Cited

OTHER PUBLICATIONS

Supplementary European Search Report in corresponding Application EP 13741207 dated Aug. 27, 2015.

Glazer et al., "Noninvasive Radiofrequency Field Destruction of Pancreatic Adenocarcinoma Xenografts Treated with Targeted Gold Nanoparticles," Clin. Cancer Res., vol. 16, No. 23, pp. 5712-5721 (Dec. 2010).

Jain et al., "Noble Metals on the Nanoscale: Optical and Photothermal Properties and some Applications in Imaging, Sensing, Biology and Medicine," Accounts of Chemical Research, vol. 41, No. 12, pp. 1578-1586 (Dec. 2008).

Li et al., "Plasmon-enhanced upconversion flourescence in NaYF4:Yb/Er/Gd nanorods coated with Au nanoparticles or nanoshells," Journal of Applied Physics, vol. 111, No. 1, pp. 14310-1-14310-7 (Jan. 2012).

Sudheendra et al., "Plasmonic Enhanced Emissions from Cubic NaYF4:Yb:Er/Tm Nanophosphors," Chem. Mater., vol. 23, No. 11, pp. 2987-2993 (Jun. 2011).

2a

2b

A.

R: any molecule

B.

C.

MULTIFUNCTIONAL NANOMATERIALS FOR THE TREATMENT OF CANCER

CROSS-REFERENCE TO RELATED APPLICATIONS

This application is the U.S. National Stage under 35 U.S.C. § 371 of International Application No.: PCT/US13/23174, filed Jan. 25, 2013, which claims the benefit of U.S. Provisional Appl. No.: 61/591,197, filed Jan. 26, 2012, the contents of which are incorporated by reference herein in their entirety.

STATEMENT REGARDING FEDERALLY SPONSORED RESEARCH OR DEVELOPMENT

This invention was made with government support under grant number CA152375 awarded by the National Institutes of Health. The government has certain rights in the invention.

BACKGROUND OF THE INVENTION

Field of the Invention

The field of the invention relates to nanomaterials, in particular, the use of multifunctional nanomaterials in the diagnosis and treatment of diseases, such as cancer.

Background

Advances in materials science have lead to the availability of nanoparticles for use in life science research. Gold is an attractive material for biomedical applications on the basis of its biocompatibility. Bhattacharya et al. *Adv Drug Deliv Rev* 60(11):1289-306 (2008). Gold nanoparticles have long been a subject of research for their unique optical properties. The collective response of the electrons, known as the plasmon, gives rise to strong optical resonance and large and fast nonlinear optical polarizability. The optical properties are well described by the classical Mie theory and are the subject of much interest for their applications in, for example, optical filters, labeling in microscopy, single-electron transistor and molecular detection via surface enhanced Raman scattering (SERS). See e.g., Bohren et al., *Adv Mater* 11:223-7 (1999); Csaki et al., *Nanotechnology* 14:1262-8 (2003); Sato et al., *J Vasc Sci Technol B* 15(1):45-8 (1997); and Nie et al., *Science* 275(5303):1102-6 (1997).

In terms of optical properties, the strong plasmon resonance of gold nanoparticles can be tuned by the size and shape of the nanoparticle. For example, the well-known 520 nm plasmon resonance of spherical shape gold nanoparticles shifted only about 25 nm to longer wavelengths as the particle size was increased from 5 to 80 nm. Adopting more complex shapes such as nanorods and nanoshells enables much wider tunability encompassing the visible and infrared region.

Specific sizes and shapes of gold nanoparticles function as near infrared absorbers, to the point of causing tissue destruction by thermal ablation. Hirsch and colleagues were among the first to specifically report the use of nanoparticle mediated thermal ablation for the destruction of tumor tissue. Hirsch et al., *Proc Natl Acad Sci USA* 100(23):13549-54 (2003). In these early studies, breast cancer cells were exposed to metal nanoshells in vitro. With the application of near infrared light (820 nm, 4 W/cm$^2$), cells linked to the nanoshells in the laser's path were ablated, while this same light had no effect on cells that had not been incubated with the nanoshells.

Additional studies have conjugated nanoparticles with antibodies to target tumor specific markers including HER2/neu24, 25 and EGFR26, 27 in an effort to "target" tumors. Loo et al., *Nano Lett* 5(4):709-11 (2005); Au et al., *ACS Nano* 2(8):1645-52 (2008); Patra et al., *Cancer Res* 68(6):1970-8 (2008); and Huang et al., *J Am Chem Soc* 128(6):2115-20 (2006). Huang et al. report on gold nanorods conjugated to anti-EGFR antibody that was cultured with both non-malignant (EGFR-negative) cells and malignant (EGFR-positive) oral epithelial cells.

Bladder cancer is a common cancer with an estimated 70,980 new cases and 14,330 deaths predicted in 2009. Most patients present with non-muscle-invasive (superficial) cancer that is initially treated with cystoscopic resection, followed by the possible addition of intravesical therapy which is administered directly into the bladder. *Bacillus* Calmette-Guerin (BCG), a live attenuated form of *Mycobacterium bovis*, is the most commonly used intravesical agent and has a proven clinical benefit in treating early-stage bladder cancer. Shelley et al., *Cochrane Database Syst Rev* 2000 (4):CD001986; and Herr et al., *J Clin Oncol* 13(6):1404-8 (1995). Despite these treatments, many patients with non-invasive bladder cancer have a recurrence, with a recent analysis of several large studies reporting a recurrence rate of 39% after BCG therapy. Kirkali et al., *Urology* 66(6 Suppl 1):4-34 (2005); and Bohle et al., *J Urol* 169(1):90-5 (2003). In patients with high risk, non-invasive bladder cancer, recurrence after BCG is very common with a recurrence rate in excess of 50%. Treatment options at recurrence include repeated intravesical BCG with our without interferon, alternative intravesical treatments such as traditional chemotherapy agents (e.g., mitomycin, doxorubicin, etc.), or radical cystectomy (bladder removal). Superficial bladder cancer may also progress to metastatic bladder cancer, which is lethal. Additionally, BCG therapy is associated with notable adverse events. An analysis of six well designed trials with BCG for superficial bladder cancer reported cystitis (67%), hematuria (23%), fever (25%), and increased urinary frequency (71%). Intravesical BCG use can uncommonly cause a systemic infection with associated caseating granulomas in distant organs such as the liver, lung, bones and vascular structures. Such dissemination requires treatment with anti-tuberculosis medication in cases with persistent findings or symptoms. A sepsis syndrome after intravesical BCG is observed rarely, but represents a potentially fatal complication.

Beyond the difficulties of treating superficial disease, the identification of recurrent disease also represents a major clinical challenge. While some tumors are exophytic (physically extending from the bladder mucosa) and easily observed visually, other tumor recurrences are flat and not easily recognized visually. In the past, random blind biopsies have been advocated to identify such lesions, although this approach is not currently deemed effective or sensitive. In addition, fluorescence endoscopy after instillation of a porphyrin (e.g. hexaminolevulinate) has also been attempted in an effort to increase tumor detection. Unfortunately, randomized clinical trials have yielded mixed and conflicting results, with 2 randomized trials failing to show a clinical benefit with the use of fluorescent endoscopy.

Epidermal growth factor receptor (EGFR) may play an important role in bladder cancer pathogenesis, in addition to other cancers. Twenty years ago, Messing and Reznikoff reported that EGF stimulated the growth of urothelial cancer cell lines in a dose-dependent fashion. Messing et al., *Cancer Res* 47(9):2230-5 (1987). Early pathologic investigations associated diffuse EGFR protein expression in urothelial cancers with increased proliferation as measured by Ki67 staining, suggesting a correlation with EGFR and the proliferation rate of urothelial cancers. Wagner et al., *Hum Pathol* 26(9):970-8 (1995). Consistent with these findings, transgenic mice with urothelial specific overexpression of EGFR develop significant urothelial hyperplasia. Cheng et al., *Cancer Res* 62(14):4157-63 (2002). More recent studies of human samples demonstrate that increased EGFR protein expression is observed in bladder cancer as compared to normal urothelium. In one case series, EGFR protein expression was noted in 2 of 15 normal urothelial samples compared with 13 of 19 patients with muscle-invasive, localized bladder cancer. Rotterud et al., *BJU Int* 95(9):1344-50 (2005). When EGFR protein is observed in normal urothelium, it is commonly in the basal portions, in contrast to its superficial (luminal) or diffuse distribution in most cancerous settings. Messing et al., *Cancer Res* 50(8): 2530-7 (1990).

There is a clear unmet medical need in the treatment and detection of non-invasive bladder cancer. Current detection methods include routine cystoscopy, oftentimes starting at the frequency of every 3 months and with decreasing frequency over time. This is used in conjunction with cytological investigation, looking for shed cancer cells, and oftentimes with fluorescent in situ hybridization (FISH), assessing for genomic changes in the shed cells as another method of detecting an active cancer. The use of these methods and the prolonged courses of retreatment have led to the identification of bladder cancer as one of the most expensive cancers to manage, which has been estimated at >$100,000 lifetime costs. Improved therapy for superficial bladder cancer therefore represents a significant current clinical need.

For these reasons, what are needed are compositions and methods for the improved detection and treatment of cancers, including bladder cancer.

SUMMARY OF THE INVENTION

Accordingly, one aspect of the present invention is to provide multifunctional nanomaterials for use in the detection and treatment of cancer, including bladder cancer.

In one embodiment, the invention provides a multifunctional nanomaterial comprising i) a nanorod comprising a noble metal, wherein the nanorod exhibits surface plasmon resonance absorption in the near-infrared spectrum; ii) an up-conversion phosphor that absorbs infrared light and emits visible luminescence; and optionally iii) a biomolecule targeting moiety.

In another aspect, the invention provides methods of treating cancer in a subject using the multifunctional nanomaterials of the invention. In some embodiments, the invention provides a method of treating cancer in a subject in need thereof, comprising: i) administering to the subject a plurality of multifunctional nanomaterials, wherein the multifunctional nanomaterial comprises 1) a nanorod comprising a noble metal, wherein the nanorod exhibits surface plasmon resonance absorption in the near-infrared spectrum; 2) an up-conversion phosphor that absorbs infrared light and emits visible luminescence; and optionally 3) a biomolecule targeting moiety, wherein the biomolecule targeting moiety selectively binds to cancer cells; ii) subjecting the cancer cells to a first intensity of near infrared light, wherein the up-conversion phosphor absorbs the near infrared light and emits visible luminescence that is detected, thereby detecting the cancer cells; and iii) subjecting the detected cancer cells of ii) to a second intensity of near infrared light, wherein the nanorod of the multifunctional nanomaterial exhibits surface plasmon resonance absorbance of the near infrared light, causing an increase in the temperature of the nanorod, wherein the increase in temperature results in thermal ablation of the cancer cells bound to the multifunctional nanomaterial, thereby treating cancer in the subject.

In another embodiment, the invention provides a method of treating cancer in a subject in need thereof, comprising: i) administering to the subject a plurality of multifunctional nanomaterials, wherein the multifunctional nanomaterial comprises 1) a nanorod comprising a noble metal, wherein the nanorod exhibits surface plasmon resonance absorption in the near-infrared spectrum; 2) an up-conversion phosphor that absorbs infrared light and emits visible luminescence; and optionally 3) a biomolecule targeting moiety, wherein the biomolecule targeting moiety selectively binds to cancer cells; ii) subjecting the cancer cells to near infrared light, wherein the up-conversion phosphor absorbs the near infrared light and emits visible luminescence that is detected, thereby detecting the cancer cells and wherein the nanorod of the multifunctional nanomaterial exhibits surface plasmon resonance absorbance of the near infrared light, causing an increase in the temperature of the nanorod, wherein the increase in temperature results in thermal ablation of the cancer cells bound to the multifunctional nanomaterials, thereby treating cancer in the subject.

In another embodiment, the invention provides a method of treating cancer in a subject in need thereof, comprising: i) administering to the subject a plurality of multifunctional nanomaterials, wherein the multifunctional nanomaterial comprises 1) a nanorod comprising a noble metal, wherein the nanorod exhibits surface plasmon resonance absorption in the near-infrared spectrum; 2) an up-conversion phosphor that absorbs infrared light and emits visible luminescence; and optionally 3) a biomolecule targeting moiety, wherein the biomolecule targeting moiety selectively binds to cancer cells; ii) subjecting the cancer cells to near infrared light, wherein the nanorod of the multifunctional nanomaterial exhibits surface plasmon resonance absorbance of the near infrared light, causing an increase in the temperature of the nanorod, wherein the increase in temperature results in thermal ablation of the cancer cells bound to the multifunctional nanomaterials, thereby treating cancer in the subject.

In another embodiment, the invention provides a method of detecting cancer in a subject in need thereof, comprising: i) administering to the subject a plurality of multifunctional nanomaterials, wherein the multifunctional nanomaterial comprises 1) a nanorod comprising a noble metal, wherein the nanorod exhibits surface plasmon resonance absorption in the near-infrared spectrum; 2) an up-conversion phosphor that absorbs infrared light and emits visible luminescence; and optionally 3) a biomolecule targeting moiety, wherein the biomolecule targeting moiety selectively binds to cancer cells; and ii) subjecting the cancer cells to near infrared light, wherein the up-conversion phosphor absorbs the near infrared light and emits visible luminescence that is detected, thereby detecting the cancer cells.

In some embodiments, the surface plasmon resonance of the noble metal nanorod enhances the efficiency of frequency up-conversion of the up-conversion phosphor. In some embodiments, the enhanced efficiency of frequency up-conversion improves detection of the cancer cells. In some embodiments, the enhancement of up-conversion efficiency is by at least about one order of magnitude.

In some embodiments of the invention, the nanorod is a gold nanorod having an aspect ratio of from about 3.5 to about 6.5. In some embodiments, the aspect ratio is about 5.0. In some embodiments, the surface plasmon resonance absorption wavelength of the nanorod is from about 800 nm to about 1200 nm. In one embodiment, the surface plasmon resonance absorption maximum is about 980 nm.

In some embodiments, the up-conversion phosphor comprises optically active donor and acceptor ions embedded in a host material. In some embodiments, the donor and acceptor ions are rare earth ions selected from the group consisting of $Yb^{3+}$, $Er^{3+}$, $Eu^{3+}$, $Tb^{3+}$, $Ce^{3+}$, $Pr^{3+}$, $Nd^{3+}$, $Gd^{3+}$, $Sm^{3+}$, $Dy^{3+}$, $Ho^{3+}$ and $Tm^{3+}$. In some embodiments, the host material is selected from the group consisting of $YF_3$, $NaYF_4$, $ZrF_4$, $AlF_3$, $BaY_2F_8$, $BaCl_2$, YOCl, and $Y_2O_3$. In one embodiment, the up-conversion phosphor is $NaYF_4$:$Yb^{3+}$,$Er^{3+}$. In some embodiments, the up-conversion phosphor absorbs infrared light with a wavelength of from about 800 nm to about 1300 nm. In one embodiment, the up-conversion phosphor absorbs infrared light with a wavelength of about 980 nm. In some embodiments, the upconversion phosphor is conjugated directly to the nanorod. In some embodiments, the upconversion phosphor is conjugated indirectly to the nanorod via a linker.

In some embodiments, the biomolecule targeting moiety comprises an antibody, peptide, polypeptide, lipid, nucleic acid, carbohydrate, aptamer and a small organic molecule. In some embodiments, the biomolecule targeting moiety is selected from the group consisting of a monoclonal antibody, a polyclonal antibody, a chimeric antibody, and a chimeric, humanized antibody. In some embodiments, the biomolecule targeting moiety is an antibody that specifically binds a biomolecule expressed on the surface of a cancer cell. In some embodiments, the cancer cell is selected from the group consisting of a bladder cancer cell, a skin cancer cell, and an oral cancer cell. In some embodiments, the biomolecule expressed on the surface of a cancer cell is a growth factor receptor. In one embodiment, the growth factor receptor is the epidermal growth factor receptor. In one embodiment, the antibody is cetuximab.

In some embodiments, the biomolecule targeting moiety is conjugated directly to the nanorod. In some embodiments, the biomolecule targeting moiety is conjugated indirectly to the nanorod via a linker. In one embodiment, the linker comprises polyethylene glycol or a functionalized derivative thereof.

It is to be understood that both the foregoing general description and the following detailed description are exemplary, and thus do not restrict the scope of the invention.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION

Figure 1A:
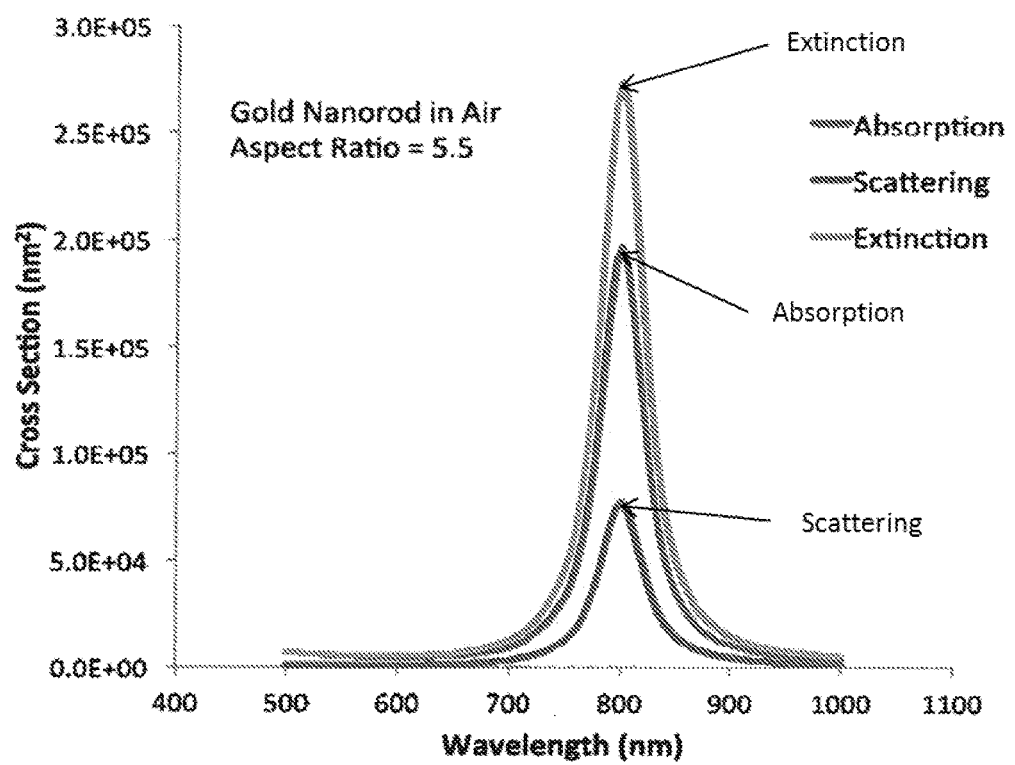
FIG. 1. Calculated extinction efficiency of nanorods with an aspect ratio of (A) 5.5 and (B) 8. Total extinction, absorption and scattering curves are indicated by arrows. The aspect ratio is the ratio of diameter to the length.

Cancer survival in most cases depends upon early diagnosis and detection of the primary tumor and aggressive surgical and/or therapeutic intervention to ensure that the cancer cells are killed and eradicated from the body. Monitoring the patient after therapy to detect any recurrence of cancer is also critical. The present invention is based on the discovery of multifunctional nanomaterials having improved properties that aid in the detection, diagnosis, and treatment of cancer. In accordance with some of the embodiments as described herein, the multifunctional nanomaterials comprise a targeting moiety that selectively binds to cancer cells, an upconversion phosphor that aids in detecting and imaging the cancer cells, and a nanorod comprising a noble metal that functions to thermally ablate the cancer cells. The multifunctional nanomaterials therefore enable the simultaneous detection and treatment of cancer, which can result in eradication of cancer cells, prevention of cancer recurrence, and prolongation of patient survival.

Reference will now be made in detail to embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, the exemplary methods, devices, and materials are now described.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of "or" means "and/or" unless stated otherwise. The use of "a" herein means "one or more" unless stated otherwise or where the use of "one or more" is clearly inappropriate. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein "about" and "approximately" mean±10% of the value indicated.

The term "aspect ratio" refers to the length divided by the width of a nanorod.

The term "biomolecule targeting moiety" refers to a substance that binds or interacts with a target biomolecule. In some embodiments, the target biomolecule is a protein receptor located on the surface of a cancer cell.

The term "noble metal" refers to metals that are resistant to corrosion and oxidation in moist air. The noble metals include ruthenium, rhodium, palladium, silver, osmium, iridium, platinum, and gold.

Figure 1B:
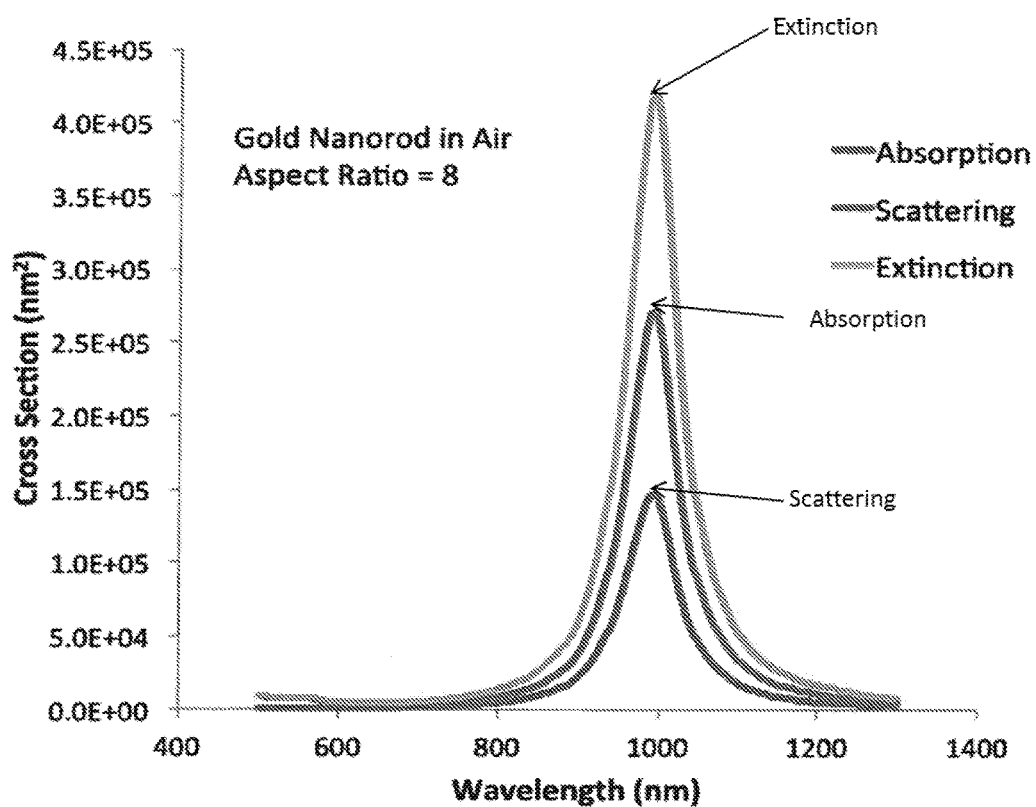

A metal "nanorod" is an anisotropic nanoparticle which exhibits two distinct plasmon resonances, one corresponding to electron oscillation along the transverse direction and another along the longitudinal direction. Since the longitudinal dimension is larger than the transverse dimension, the longitudinal plasmon has a lower frequency or longer wavelength. Thus, it is possible to shift the plasmon resonance by controlling the length of the nanorods. FIG. 1 shows the extinction spectra of gold nanorods calculated by the discrete dipole approximation method. Draine BT. The Discrete-Dipole Approximation for Light Scattering by Irregular Targets. In: Mishchenko M I, Hovenier J W, Travis L D, eds. Light Scattering by Nonspherical Particles: Theory, Measurements, and Geophysical Applications. New York: Academic Press, 131-45 (2000). The higher aspect ratio, which corresponds to longer rods, exhibits plasmon resonance peak at a longer wavelength. Chen et al. *J Phys Chem B* 109(42):19553-5 (2005). It has been shown that the peak can be shifted to over 1 μm in wavelength. It should be noted that the possible tuning range contains the so-called water window (800-1300 nm) where water absorption is weak and the physiological transmissivity is high. Another important characteristic (FIG. 1) is that the light extinction is primarily due to absorption with very little scattering. This enables strong absorption by the nanorods to produce local cellular hyperthermia.

In some embodiments, the invention provides a multifunctional nanomaterial with distinct functions. In some embodiments, the invention provides a multifunctional nanomaterial comprising i) a nanorod comprising a noble metal, wherein the nanorod exhibits surface plasmon resonance absorption in the near-infrared spectrum; ii) an up-conversion phosphor that absorbs infrared light and emits visible luminescence; and optionally iii) a biomolecule targeting moiety. In some embodiments, the surface plasmon resonance of the noble metal nanorod enhances the efficiency of frequency up-conversion of the up-conversion phosphor, which can improve detection of the nanomaterials.

Nanorods

One component of the nanomaterials is a nanorod comprising a noble metal exhibiting surface plasmon resonance. In some embodiments, the noble metal nanorod exhibits surface plasmon resonance in the near-infrared spectrum where physiological absorption is low. When the nanorod size is small, absorption dominates the surface plasmon resonance, leading to strong absorption band at the plasmon resonance wavelength. In some embodiments, most of the absorbed energy is dissipated in heat. The resultant local heating can be to kill disease cells, enabling a laser-induced photothermal ablation therapy.

In some embodiments, the nanorod is made from a noble metal selected form the group consisting of ruthenium, rhodium, palladium, silver, osmium, iridium, platinum, and gold. In some embodiments, the nanorod is made from a noble metal alloy.

In one embodiment, the nanorod is a gold nanorod. Various methods can be used to make gold nanorods, for example, the seeding growth method as described by Jana et al., *J. Phys. Chem. B* 105:4065-4067 (2001). Gold nanorods can also be prepared using electrochemical and photochemical reduction methods in aqueous surfactant media, porous alumina templates, polycarbonate membrane templates, and carbon nanotube templates. See, e.g., Yu et al., *J. Phys. Chem. B* 101:6661 (1997); Esumi et al., *Langmuir* 11:3285 (1995); Martin et al, *ADV. Mater.* 11:1021 (1999); van der Zande et al., *Langmuir* 16:451 (2000); Cepak et al., *J. Phys. Chem. B* 102:9985 (1998); Govindaraj et al., *Chem. Mater.* 12:202 (2000); and Fullam et al., *AdV. Mater.* 12:1430 (2000). Exemplary syntheses of gold nanorods are also described below in Example 1.

In some embodiments, the nanorod exhibits surface plasmon resonance absorption in the near-infrared spectrum when exposed to a source of near infrared light. The near infrared spectrum refers to wavelengths of light from about 700 nm to about 1800 nm. In some embodiments, the surface plasmon resonance absorption of the nanorod is from about 700 to about 1500, from about 800 nm to about 1300 nm, from about 850 nm to about 1200 nm, from about 900 nm to about 1050 nm, and from about 950 nm to about 1000 nm. In some embodiments, the nanorod exhibits surface plasmon resonance absorption at about 980 nm.

In some embodiments, the nanorod has an aspect ratio of from about 2 to about 12, from about 3.5 to about 6.5, from about 4.0 to about 6.0, or from about 4.5 to about 5.5. In some embodiments, the aspect ratio is about 5.0. As the aspect ratio of the nanorod increases, the maximum absorption wavelength of the nanorod also increases. By changing the dimensions of the nanorods, the surface plasmon absorption band can be tuned to various wavelengths, such as the near infrared region where light penetration through tissues is optimal and minimal tissue damage is expected to occur. In some embodiments, the near infrared wavelength range is not substantially absorbed by the skin or body tissues, which enables heating of the nanorod and highly localized and targeted thermal ablation without significant damage to nearby cells and tissues.

In some embodiments, the nanorod is coated with a material, for example a polymer that inhibits aggregation of the nanorod and may also facilitate conjugation to other particles, such as the upconversion phosphor and/or biomolecule targeting moiety. In some embodiments, the nanorod is coated with a substance selected from the group consisting of CTAB and polyethylene glycol (PEG). Other natural or synthetic polymers can be used as coating materials. In some embodiments, the nanorod is coated with poly(maleic anhydride-alt-octadecene) (PMAO). In some embodiments, the polymer, such as PMAO can be further grafted with other molecules, for example, poly(ethylene glycol) (PEG) or methoxyethylamine to create PMAO-PEG or PMAO-methoxyethylamine coated nanorods.

In some embodiments, the nanorod can be further conjugated to one or more chemotherapeutic agents to aid in the killing of cancer cells. Examples of chemotherapeutic agents include 5-fluorouracil, bleomycin, busulfan, camptothecin, carboplatin, chlorambucil, cisplatin (CDDP), cyclophosphamide, dactinomycin, daunorubicin, doxorubicin, etoposide (VP 16), farnesyl-protein transferase inhibitors, gemcitabine, ifosfamide, mechlorethamine, melphalan, mitomycin, navelbine, nitrosurea, plicomycin, procarbazine, taxol, temazolomide, transplatinum, vinblastine and methotrexate, vincristine, or analogs or derivatives thereof.

Upconversion Phosphor

In accordance with the invention, the multifunctional nanomaterials comprise an upconversion phosphor which is used for imaging and detection of the multifunctional nanomaterials in vivo. In some embodiments, the upconversion phosphor is conjugated to the nanorod.

In some embodiments, the upconversion phosphor absorbs infrared light and emits visible luminescence. In some embodiments, the frequency up-conversion process is based on the Förster energy transfer process. In some embodiments, the phosphor material in which this process occurs typically consists of two species of optically active ions embedded in a transparent host material. One of the two species of optically active ions, often called the donor ion, absorbs incident photons and subsequently excites the other species through the Förster energy transfer process. The other species of optically active ion, generally referred to as the acceptor ion, receives energy twice from two different donor ions and ends up at a high energy excited state from which it decays radiatively, emitting up-converted luminescence.

In some embodiments, the donor and acceptor ions are rare earth ions. In some embodiments, the transparent host materials are generally oxides, fluorides, chlorides, oxyfluorides and oxychlorides which have large enough band gap to make them transparent to the light wavelengths where the embedded ions absorb and emit. Alternatively, in some embodiments, this process can occur in an organic material containing chromophores in such a way that two chromophores absorb incident photons and subsequently transfer the energy to a core where the energies are combined to create a high energy excitation, which subsequently radiates up-converted luminescence. In this case, organic nanoparticles such as dendrimers can be used instead of inorganic nanoparticles.

Advantageously, it has also been discovered that if the plasmon resonance absorption of the nanorod occurs at the same wavelength where the electronic processes responsible for frequency up-conversion in the up-conversion phosphor occur, the local field enhancement due to the strong surface plasmon resonance can enhance the efficiency of the frequency upconversion process in the up-conversion phosphors, resulting in strongly enhanced up-converted luminescence. The rate of Förster energy transfer process responsible for the frequency up-conversion depends on the radiative transition rate which can be modified by the strongly enhanced local field due to surface plasmon resonance. In some embodiments, the enhanced frequency upconversion efficiency can facilitate improved targeting and detection of cancer cells using a near infrared source. In some embodiments, at least one order of magnitude improvement in up-conversion efficiency is achieved. In some the frequency upconversion efficiency is improved by at least 25%, at least 50%, at least 75%, at least 100%, at least 250%, at least 500%, at least 750% or at least 1000%.

In some embodiments, the upconversion phosphor nanoparticle is about 20-500 nm in size. In some embodiments, the upconversion phosphor nanoparticle is about 500 nm, about 400 nm, about 300 nm, about 200 nm, about 100 nm, about 90 nm, about 80 nm, about 70 nm, about 60 nm, about 50 nm, about 40 nm, about 30 nm, or about 20 nm in size. In some embodiments, the upconversion phosphor is about 30-40 nm in size.

In some embodiments, the upconversion phosphor is a rare earth ion doped oxide, fluoride, chloride, oxyfluoride or oxychloride. In some embodiments, the rare earth ions could be any of the lanthanide and actinide elements. In some embodiments, the rare earth ions are selected from the group consisting of $Yb^{3+}$, $Er^{3+}$, $Eu^{3+}$, $Tb^{3+}$, $Ce^{3+}$, $Pr^{3+}$, $Nd^{3+}$, $Gd^{3+}$, $Sm^{3+}$, $Dy^{3+}$, $Ho^{3+}$, $Tm^{3+}$, and combinations thereof. Oxides are binary compounds of metal oxides or ternary compounds made of rare earth, alkali or alkaline earth metal and oxygen. Fluorides are binary compounds of metal fluorides or ternary compounds comprised of rare earth, alkali or alkaline earth metal and fluorine. Chlorides are binary compounds of metal chlorides or ternary compounds comprised of rare earth, alkali or alkaline earth metal and chlorine. In some embodiments, the host material is selected from the group consisting of $YF_3$, $YNaF_4$, $ZrF_4$, $AlF_3$, $BaY_2F_8$, $BaCl_2$, $YOCl$, and $Y_2O_3$.

In some embodiments, the upconversion phosphor is selected from $NaYF_4:Yb^{3+},Er^{3+}$, $SrF_2:Er^{3+}$, $YF_3:Yb^{3+},Tb^{3+}$, $YbPO_4:Yb^{3+},CaF_2:Eu^{2+}$, $YF_3:Yb^{3+},Tm^{3+}$, $NaYF_4:Yb^{3+}$, $Tm^{3+}$, $Na_2Y_3F_{11}:Yb^{3+},Er^{3+}$, $YF_3:Yb^{3+},Er^{3+}$, $SrCl_2:Yb^{3+}$ and $SrCl_2:Yb^{3+},Tb^{3+}$. The upconversion phosphor material absorbs at various wavelengths of infrared light and converts it into visible fluorescence via a cooperative energy transfer process, for example, in the case of $NaYF_4:Yb^{3+},Er^{3+}$, between the $Yb^{3+}$ and $Er^{3+}$ ions.

In some embodiments, the upconversion phosphor absorbs light at a wavelength of from about 800 nm to about 1050 nm. In some embodiments, the upconversion phosphor absorbs at a wavelength of about 980 nm. In some embodiments, the upconversion phosphor absorbs at a wavelength that overlaps or is about the same as the surface plasmon absorption wavelength of the nanorod of the multifunctional nanomaterial. In some embodiments, the upconversion phosphor is $NaYF_4:Yb^{3+},Er^{3+}$ and is conjugated to a gold nanorod.

In some embodiments, the ratio of upconversion phosphor to nanorods in the multifunctional nanomaterials is about 0.10:1, about 0.25:1, about 0.50:1, about 1:1, about 2:1, about 3:1, about 4:1, about 5:1, about 6:1, about 7:1, about 8:1, about 9:1 or about 10:1 or more.

In some embodiments, the upconversion phosphor is coated with a material, for example a polymer that aids in inhibiting aggregation. In some embodiments, the upconversion phosphor is coated with poly(maleic anhydride-alt-octadecene) (PMAO). In some embodiments, the polymer, such as PMAO can be further grafted with other molecules, for example, poly(ethylene glycol) (PEG) or methoxyethylamine to create PMAO-PEG or PMAO-methoxyethylamine coated particles. In some embodiments, other natural or synthetic polymers can be used as coating materials.

In some embodiments, poly(ethylene glycol) (PEG) is used as a linker to conjugate the upconvesion phosphor and the nanorod. The upconversion phosphor can be obtained from commercial sources, such as, for example, Phosphor Tech Corp (Atlanta, Ga.). The upconversion phosphor particles commercially available are typically synthesized in organic solvent and therefore, in some embodiments, the upconversion phosphor particles are processed to make them more water soluble. In some embodiments, the upconversion phosphor is treated with acid, such as HCl to remove surface oleic acid. In some embodiments, the upconversion phosphor is further coated to aid in conjugation to the nanorod. In some embodiments, the upconversion phosphor is silica nanocoated.

In some embodiments, the upconversion phosphor particles are grafted with bi-functional PEG with thiol groups which serve as binding sites for the noble metal, such as gold, on the nanorods. The PEGylated upconversion phosphor nanoparticles can be mixed with gold nanorods to form an upconversion phosphor-nanorod complex.

Biomolecule Targeting Moiety

In accordance with some embodiments of the invention, the multifunctional nanomaterials comprise one or more biomolecule targeting moieties. In some embodiments, the biomolecule targeting moiety is specific for a single biomolecule. In some embodiments, a plurality of different biomolecule targeting moieties are present in the multifunctional nanomaterials. In some embodiments, the plurality of biomolecule targeting moieties recognize one or more biomolecules. In some embodiments, the one or more biomolecules are markers for certain cancer cells.

In some embodiments, the ratio of biomolecule targeting moieties to nanorods in the multifunctional nanomaterials is about 1:1, about 2:1, about 3:1, about 4:1, about 5:1, about 6:1, about 7:1, about 8:1, about 9:1, about 10:1, about 15:1, about 20:1, about 30:1, about 40:1, about 50:1, about 75:1 or about 100:1 or more.

In some embodiments, the biomolecule targeting moiety is selected from the group consisting of an antibody, an antigen-binding antibody fragment, a small organic molecule, a polypeptide, an oligonucleotide, an aptamer, a lipid, or a carbohydrate.

In some embodiments, the biomolecule targeting moiety comprises an antibody. In some embodiments, the antibody can be monoclonal, polyclonal, chimeric, humanized, single-chain, or antigen-binding fragments thereof. The antibody can be raised against a particular biomolecular protein or antigen according to any of the methods known in the art. For example, the antibodies can be raised in polyclonal form by methods known in the art, or alternatively, in monoclonal form using, for example, known hybridoma technology. The antibodies can be raised in any suitable mammal, including, for example, rabbits, guinea pigs, rats, mice, horses, sheep, goats, and primates. In some embodiments, the antibodies are recombinantly produced. In some embodiments, the antibodies are derived from mice. In some embodiments, the antibodies are humanized by methods known in the art for the purpose of human clinical use. In some embodiments, the antibody is of the IgG class, but can be of any of the other classes, including IgM, IgA, IgD or IgE. The antibody can also be of any subclass, e.g., the IgGi, $IgG_2$, $IgG_3$, and $IgG_4$ subclasses. In some embodiments, the biomolecule targeting moiety is a secondary antibody that binds to a first antibody that targets the biomolecule. Examples of secondary antibodies include, for example, goat anti-rabbit, goat anti-mouse, sheep anti-mouse, sheep anti-rabbit, rabbit anti-mouse, and rabbit anti-sheep. The antibody can be of any class including IgG, IgM, IgA, IgD or IgE. The antibody can also be of any subclass.

In some embodiments, the antibody is an antibody fragment that contains at least a portion of a hypervariable ($F_v$) region of a biomolecule targeting antibody. In some embodiments, the antibody fragment has binding characteristics that are the same as, or comparable to, those of the whole antibody. Some examples of suitable antibody fragments include any fragment that comprises a sufficient portion of the hypervariable region to bind specifically, and with sufficient affinity, to the biomolecule of interest. Such fragments can be, for example, a Fab or $(Fab)_2$ fragment. These fragments can be derived from the whole antibody by techniques well-known in the art, such as, for example, by use of enzymatic cleavage (e.g., papain or pepsin at hinge locations) followed by chemical reduction. In some embodiments, the antibody fragments contain all six complementarity determining regions (CDRs) of the whole antibody, although functional fragments containing fewer than all of such regions, such as three, four or five CDRs, can also be used.

In some embodiments, the antibody is generated by an immunological response to a recombinant biomolecule protein, for example, a cell receptor protein or fragment thereof. The generated antibodies can be harvested by conventional immunological methods known in the art.

In some embodiments, the biomolecule targeting moiety is a peptide or receptor-specific ligand. The receptor-specific ligand can be a natural or synthetic molecule which specifically binds to a receptor on the surface of a cell. Examples of natural molecules include growth factors, hormones, and neurotransmitters.

In some embodiments, the biomolecule targeting moiety specifically binds to a target biomolecule substance, for example a receptor protein at the surface of a cell. In some embodiments, the cell is a cancerous cell. In some embodiments, the biomolecule is a receptor that is overexpressed on the cancer cell or is a marker for the cancer cell.

In some embodiments, the biomolecule is an epidermal growth factor receptor (EGFR), and the biomolecule targeting moiety is an epidermal growth factor receptor antibody. In some embodiments, the EGFR antibody is ERBITUX (cetuximab).

Conjugation

The components of the multifunctional nanomaterials are conjugated. In some embodiments, the upconversion phosphor and the biomolecule targeting moiety is conjugated to the nanorod. The conjugation of the components can be either direct or indirect (e.g., they can be connected via one or more linker substances or coatings). The biomolecule targeting moiety and the up-conversion phosphor can be conjugated to the nanorod by any suitable means which retains the functional properties of each component. In some embodiments, the conjugation results in the permanent attachment of the nanorod to the biomolecule targeting moiety and the up-conversion phosphor. Methods for conjugating substances to nanoparticles are known in the art and include conjugation via electrostatic charges or covalent bonding. See, e.g., Sokolov et al., *Technology in Cancer Research & Treatment* 2(6):491-504 (2003). Conjugation of an antibody to a gold nanorod is described in Example 2 and conjugation of an upconversion phosphor and a gold nanorod is described in Example 7, below.

In some embodiments, the biomolecule targeting moiety and/or the upconversion phosphor is bound to the nanorod by one or more covalent bonds. In some embodiments, the biomolecule targeting moiety and/or the upconversion phosphor is bound to the nanorod by non-covalent interactions. Some examples of other bonding modes include ionic bonding, hydrogen bonding, metal-coordination, and dative bonding.

In some embodiments, the biomolecule targeting moiety and/or upconversion phosphor is bound indirectly to the nanorod via one or more linking molecules or materials (e.g., linkers or crosslinkers). The linker can be any suitable molecular moiety or material capable of keeping the biomolecule targeting moiety and/or upconversion phosphor bound to the nanorod. The linker can be, for example, a suitable biological or synthetic molecule or material. Some examples of biological materials that can function as linkers include proteins and glycoproteins (e.g., protein A, antibodies, albumin, and enzymes), polysaccharides, nucleic acids, lipids, glycolipids, lipoproteins, and the like.

In some embodiments, the linkers can include synthetic linkers. In some embodiments the synthetic linker is PEG or a functionalized PEG, for example, OPSS-SPEG-SVA (MW: 5000) (Laysan Bio, Arab, Ala.). In some embodiments, thiol-functionalized PEG can be used. In some embodiments, the biomolecule targeting moiety and the up-conversion phosphor is conjugated to the nanorod using polyethylene glycol (PEG) or a functionalized PEG as a linker. See, e.g., Patra et al., *Cancer Res* 68(6):1970-8 (2008).

Other linkers which can be employed include siloxanes (i.e., "chemically functionalized silica"), polysiloxanes, polyvinyl alcohol (PVA), polyvinyl acetate (PVAc), the polyacrylates and polymethacrylates, fluoropolymers, liposomes, dendrimers, the dextrans, cellulosic materials, and the like. In some embodiments, the synthetic linkers contain two functional groups: one for binding to the nanorod, and another for binding to the biomolecule targeting moiety and/or upconversion phosphor.

In some embodiments, the nanorod, the biomolecule targeting moiety and/or the upconversion phosphor is coated with a substance that binds to a linker. In some embodiments, the nanorod or the upconversion phosphor is coated with a silica based coating.

In some embodiments, the conjugation of the nanorods and up-conversion phosphor is done in such a way that they do not interfere destructively. For example, metal surfaces can quench luminescence if the luminescent material is too close to the metal surface. In some embodiments, the complex nanomaterial made of plasmonic nanomaterial and up-conversion phosphor has a nanometric gap between the two. In some embodiments, this can be achieved by applying nanoscale coating of organic or inorganic material on one of the two components. Examples of such coating materials are silica and organic polymers such as poly(ethylene)glycol. In some embodiments, the separation between the two nanomaterials is precisely controlled.

In some embodiments, the multifunctional nanomaterials can be further conjugated with other functional materials to expand functionality.

Methods of Detection and Treatment

In some embodiments, the invention provides methods of treating cancer in a subject in need of treatment using the multifunctional nanomaterials of the invention. In one embodiment, the invention provides a method of treating cancer in a subject in need thereof, comprising: i) administering to the subject a plurality of multifunctional nanomaterials, wherein the multifunctional nanomaterial comprises 1) a nanorod comprising a noble metal, wherein the nanorod exhibits surface plasmon resonance absorption in the near-infrared spectrum; 2) an up-conversion phosphor that absorbs infrared light and emits visible luminescence; and optionally 3) a biomolecule targeting moiety, wherein the biomolecule targeting moiety selectively binds to cancer cells; ii) subjecting the cancer cells to a first intensity of near infrared light, wherein the up-conversion phosphor absorbs the near infrared light and emits visible luminescence that is detected, thereby detecting the cancer cells; and iii) subjecting the detected cancer cells of ii) to a second intensity of near infrared light, wherein the nanorod of the multifunctional nanomaterial exhibits surface plasmon resonance absorbance of the near infrared light, causing an increase in the temperature of the nanorod, wherein the increase in temperature results in thermal ablation of the cancer cells bound to the multifunctional nanomaterials, thereby treating cancer in the subject.

In another embodiment, the invention provides a method of treating cancer in a subject in need thereof, comprising: i) administering to the subject a plurality of multifunctional nanomaterials, wherein the multifunctional nanomaterial comprises 1) a nanorod comprising a noble metal, wherein the nanorod exhibits surface plasmon resonance absorption in the near-infrared spectrum; 2) an up-conversion phosphor that absorbs infrared light and emits visible luminescence; and optionally 3) a biomolecule targeting moiety, wherein the biomolecule targeting moiety selectively binds to cancer cells; ii) subjecting the cancer cells to near infrared light, wherein the up-conversion phosphor absorbs the near infrared light and emits visible luminescence that is detected, thereby detecting the cancer cells and wherein the nanorod of the multifunctional nanomaterial exhibits surface plasmon resonance absorbance of the near infrared light, causing an increase in the temperature of the nanorod, wherein the increase in temperature results in thermal ablation of the cancer cells bound to the multifunctional nanomaterials, thereby treating cancer in the subject.

In another embodiment, the invention provides a method of treating cancer in a subject in need thereof, comprising: i) administering to the subject a plurality of multifunctional nanomaterials, wherein the multifunctional nanomaterial comprises 1) a nanorod comprising a noble metal, wherein the nanorod exhibits surface plasmon resonance absorption in the near-infrared spectrum; 2) an up-conversion phosphor that absorbs infrared light and emits visible luminescence; and optionally 3) a biomolecule targeting moiety, wherein the biomolecule targeting moiety selectively binds to cancer cells; ii) subjecting the cancer cells to near infrared light, wherein the nanorod of the multifunctional nanomaterial exhibits surface plasmon resonance absorbance of the near infrared light, causing an increase in the temperature of the nanorod, wherein the increase in temperature results in thermal ablation of the cancer cells bound to the multifunctional nanomaterials, thereby treating cancer in the subject.

In another embodiment, the invention provides a method of detecting cancer in a subject in need thereof, comprising: i) administering to the subject a plurality of multifunctional nanomaterials, wherein the multifunctional nanomaterial comprises 1) a nanorod comprising a noble metal, wherein the nanorod exhibits surface plasmon resonance absorption in the near-infrared spectrum; 2) an up-conversion phosphor that absorbs infrared light and emits visible luminescence; and optionally 3) a biomolecule targeting moiety, wherein the biomolecule targeting moiety selectively binds to cancer cells; and ii) subjecting the cancer cells to near infrared light, wherein the up-conversion phosphor absorbs the near infrared light and emits visible luminescence that is detected, thereby detecting the cancer cells.

In some embodiments, the multifunctional nanomaterials target cancer cells. The targeting can be done passively by the leaky vasculatures many tumors exhibit or actively by coating the nanorod with one or more biomolecule targeting moieties that bind specifically to targeted biomolecules. In some embodiments, the targeting moieties are antibodies for proteins or cell surface receptors. In some embodiments, the biomolecule targeting moiety binds a cancer specific biomarker.

Once the multifunctional nanomaterials are properly attached to the targeted cells, they can be illuminated by laser light tuned to the plasmon resonance wavelength of the nanorod. The energy of the near infrared laser illumination can vary, depending on the environment being illuminated, the intensity desired, and whether the purpose is for detection and imaging or targeted thermal ablation. The determination of laser intensity to suit a specific application can be determined experimentally by an ordinary artisan. In some embodiments, the laser intensity used to illuminate the multifunctional nanomaterials is less than about 75 $W/cm^2$, less than about 60 $W/cm^2$, less than about 50 $W/cm^2$, less than about 40 $W/cm^2$, less than about 30 $W/cm^2$, less than about 30 $W/cm^2$, less than about 20 $W/cm^2$, less than about 10 $W/cm^2$, or less than about 5 $W/cm^2$. The resultant local heating kills the cells to which the nanomaterials are attached. In some embodiments, the heating can be confined into a highly localized area and the local heating can be precisely controlled by the light dose, i.e. the intensity and duration of light exposure. In some embodiments, the localized heating is achieved by using nanoscale materials that support surface plasmon resonance and by focusing the laser beam into a small spot. In some embodiments, the surface plasmon resonance is tuned, by controlling the size and shape of the nanomaterial, to a wavelength in the near-infrared region where physiological transmissivity is the highest. In some embodiments, absorption by the background tissues is minimized and therefore the heating occurs only in the immediate vicinity of the nanomaterials and any collateral damage to untargeted cells and tissues is minimized.

In some embodiments, the same light source can be used to excite both the nanorod and up-conversion phosphor so that one may achieve local heating for killing disease cells with photothermal ablation therapy while monitoring the cells simultaneously with visible fluorescence imaging. In some embodiments, the cells are illuminated with a first intensity near infrared light that is strong enough to permit cell visualization but not thermal ablation. Once the cells are identified and localized, in some embodiments, the detected cells are illuminated with a second intensity near infrared light that is powerful enough to result in thermal ablation of the cells. Following thermal ablation, the cells can be further visualized to assess the status of the cells, and if needed, further illuminated with infrared light to thermally ablate the cells.

Thus, in some embodiments, the invention enables a new treatment technique that provides photothermal therapy with in situ, real-time monitoring. As indicated above, the surface plasmon resonance of the nanorod can enhance the efficiency of frequency upconversion of the upconversion phosphor, which can improve the sensitivity of detection and imaging of cancer cells, resulting in improved diagnosis and treatment of cancer.

In some embodiments, the use of up-conversion phosphor for fluorescence imaging has a unique advantage of having extremely low background. Because the excitation light falls within the near infrared spectrum where the background absorption by the tissues and cells is minimal, this method can produce high-contrast images even with low intensity fluorescence in some embodiments.

In some embodiments, one or more semiconductor quantum dots can be added which absorb over a broad spectrum and emit at the same wavelength where the plasmon enhancement of up-conversion occurs. The up-conversion phosphors based on rare earth ions typically exhibit narrow absorption band and therefore their overall absorption cross-section is not high. In contrast, semiconductor quantum dots exhibit broad and strong absorption band at energies above their band gap. In some embodiments, the absorption characteristics of up-conversion phosphors are significantly enhanced by coupling them with semiconductor quantum dots. In this multifunctional nanomaterial, light over a broad range of energy is absorbed by the quantum dot, which subsequently emit at the wavelength corresponding to its exciton energy. If the quantum dot is designed in such a way that the emission energy coincides with the absorption line of the upconversion phosphor, the light emitted by the quantum dot will be absorbed by the upconversion phosphor and thus contribute to up-converted luminescence. In some embodiments, quantum dots may be made of II-VI compound semiconductors such as CdSe, CdS, ZnS, PbS or III-V compounds like InAs, InP, GaP, and GaN. In some embodiments, this results in significant enhancement in up-conversion efficiency. The coupling between quantum dot and upconversion phosphor can be either radiative (i.e. the quantum dot emits a photon and the up-conversion phosphor absorbs it) or non-radiative through the Förster energy transfer process.

Figure 5:
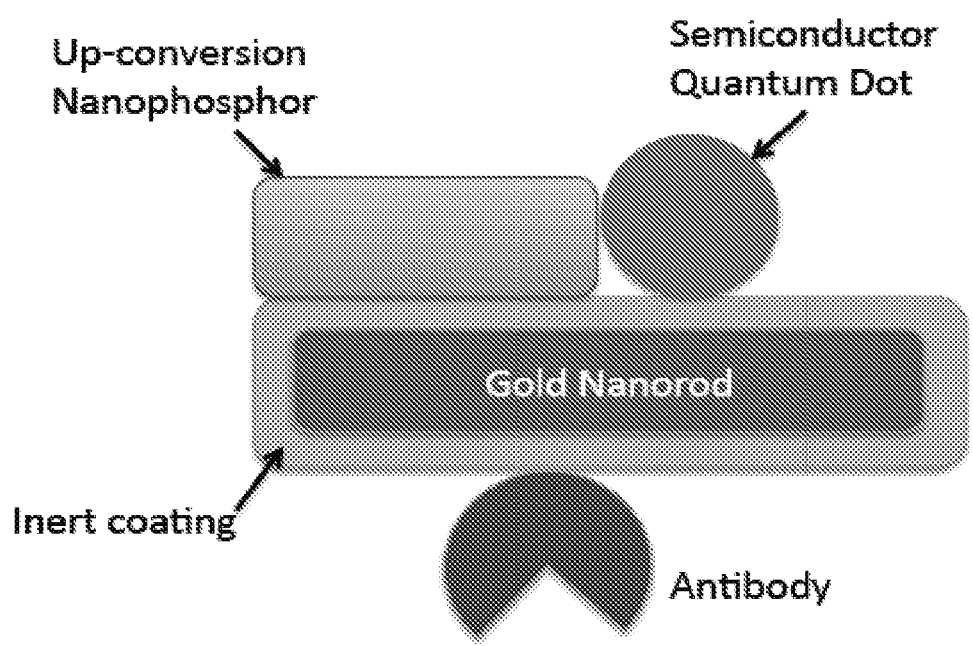
FIG. 5. Schematic drawing of one embodiment of multifunctional nanomaterial, which is comprised of a gold nanorod for local heating and field enhancement, an up-conversion phosphor for visible luminescence under infrared excitation, a semiconductor quantum dot for broadband absorption and an antibody for cell targeting.

FIG. 5 shows a schematic drawing of one embodiment of a multifunctional nanomaterial, which is comprised of a gold nanorod exhibiting strong plasmon resonance in the near-infrared region, an up-conversion phosphor absorbing the near-infrared light and emitting visible luminescence, a semiconductor quantum dot with broad absorption band and an antibody for specific binding with a targeted protein. In some embodiments, the gold nanorod has a nanometrically thin inert coating so as not to quench luminescence from the up-conversion phosphor and quantum dot. The inert coating can also help enhance the colloidal stability and reduce toxicity.

In some embodiments, the cancer to be treated or detected is selected from the group consisting of bladder cancer, skin cancer and oral cancer. In one embodiment, the cancer is invasive bladder cancer. In some embodiments, recurrence of invasive bladder cancer is detected and treated in accordance with the methods of the invention.

In one embodiment of the method to treat or detect cancer, the multifunctional nanomaterial comprises a gold nanorod, upconversion phosphor and epidermal growth factor receptor (EGFR) antibody.

In some embodiments, the gold nanorod is tuned to exhibit strong surface plasmon resonance at a wavelength of about 980 nm where tissue absorption is minimal and thus there would be little to no effect on normal tissue. Contrasting this, when illuminated with a 980 nm laser beam, the nanorod strongly absorbs the energy and consequently produces local heating—enough to kill the cancer cells they are specifically bound to. In some embodiments, the upconversion phosphor nanoparticle absorbs the 980 nm light and emits visible (red and green) fluorescence. This allows direct imaging of cancer cells which are generally difficult to identify with simple visual inspection. In some embodiments, since the excitation light is in the infrared spectrum where the tissues are transparent, there will be no background autofluorescence, which is commonly present in the conventional fluorescence imaging. Thus, in some embodiments, high-contrast easily identifiable fluorescence images can be obtained.

The multifunctional nanomaterials can be formulated with one or more pharmaceutically acceptable carriers or excipients prior to administration to a patient. The nanomaterials can be formulated in dosage forms suitable for delivery to the bladder. In some embodiments, the multifunctional nanomaterials are formulated for transdermal or mucosal delivery. See, e.g., *Remington's Pharmaceutical Sciences,* 18th ed., Mack Publishing, Easton, Pa. (1990).

In some embodiments, a plurality of the multifunctional nanomaterials are delivered via a urinary catheter to detect and/or treat superficial bladder cancer. Delivery via the urinary catheter allows for the direct delivery of the nanomaterials to the site of disease and avoiding systemic delivery.

In some embodiments in the treatment of bladder cancer, the laser beam is delivered via a modified cystoscope, similar to cystoscopes currently used in medical practice, precisely targeting the treatment area. In some embodiments, the same laser beam is used for both imaging the cells (at low power level) and treatment (at high power level), enabling improved detection and targeted thermal ablation treatment in one procedure.

In some embodiments, the subject to be treated or diagnosed is a mammal, such as a human. Other mammalian subjects include, but are not limited to dogs, cats, horses, cows, monkeys, gorillas, sheep, mice, rats, guinea pigs, and the like. In some embodiments, the subject is a human patient at risk for bladder cancer. In some embodiments, the subject is a human patient who is being screened for cancer, such as bladder cancer. In some embodiments, the patient has been treated for bladder cancer and is at risk for bladder cancer recurrence.

In some embodiments, the subject is a patient with high-risk, superficial bladder cancer (T1 or higher grade disease) who has been treated previously, for example, with intravesical BCG. Such patients can be screened in accordance with the detection and treatment methods as described herein, for example, every 3-6 months for the first few years after treatment. The multifunctional nanomaterials can be delivered with a cystoscope, in accordance with existing practices in the treatment and detection of bladder cancer.

While the invention has been described with reference to certain particular examples and embodiments herein, those skilled in the art will appreciate that various examples and embodiments can be combined for the purpose of complying with all relevant patent laws (e.g., methods described in specific examples can be used to describe particular aspects of the invention and its operation even though such are not explicitly set forth in reference thereto). Examples of the products and processes of the invention appear in the following non-limiting Examples.

EXAMPLES

Example 1
Gold Nanorod Synthesis

We prepared highly uniform gold nanorods by the wet chemistry route. See, e.g., Jana et al. *J Phys Chem B* 105(19):4065-7 (2001). In this method, a solution of gold seed particles is first prepared by reducing gold ions in the presence of cetryltrimethylammonium bromide (CTAB) and sodium borhydride ($NaBH_4$). The small seed particles (typically ~4 nm in size) are then mixed with the growth solution in which the seed particles undergo rod growth in the soft template of CTAB.

In this method, a solution of gold seed particles is first prepared by reducing gold ions in the presence of cetryltrimethylammonium bromide (CTAB) and sodium borhydride ($NaBH_4$). The small seed particles (typically ~4 nm in size) are then mixed with the growth solution in which the seed particles undergo rod growth in the soft template of CTAB.

Preparation of Nanorods Exhibiting Plasmon Resonance at 800 nm.

The synthesis of these nanorods can be conducted in 3 main steps and the aqueous solutions of each chemical are made as instructed. Solution (4) can be used as a stock solution and solutions (1), (2), (3), and (5) need to be made fresh every time.

A. Gold Seed Solution Preparation

Solution (1): 1.75 g CTAB is added to 48 ml water in a 50 ml centrifuge tube.

After addition of the CTAB, the tube is shaken so that a gel won't form at the bottom. The tube is sonicated for a few minutes and placed in a hot water bath (e.g., set at '3.5' on a heat plate) until CTAB is fully dissolved. The solution is cooled at room temperature. The solution should be used as soon as possible when it gets to room temperature.

Solution (2): 0.8 ml of gold stock solution is added to 1.92 ml of water.

The gold ion source can be, for example, $HAuCl_4$ or $NaAuCl_4$. The concentration of the gold stock solution is 0.025 M. 7.5 ml of solution (1) is placed in a 15 ml plastic tube, followed by addition of 250 µl of solution (2). The tube is mixed gently by the inversion of the tube.

Solution (3): 0.023 g $NaBH_4$ is added to 600 µl of ice-cold water.

In a separate microcentrifuge tube, 6 µl of solution (3) is added to 594 µl of water. The 600 µl of diluted $NaBH_4$ solution is then added to the 15 ml centrifuge tube above and mixed for 2 minutes on nutator.

These steps should result in a pale brown solution. This gold seed solution is stored in a ~25° C. water bath until further use.

B. Growth Solution Preparation

Solution (4): $AgNO_3$ 0.0169 g in 1 mL $DDH_2O$.

Solution (5): Ascorbic Acid 0.0352 g in 2 mL $DDH_2O$.

To prepare the growth solution, in a 50 ml plastic tube, 40 ml of solution (1) is poured and added to 1.7 ml of solution (2). The tube is gently inverted, and then diluted $AgNO_3$ solution is added (25 µl of solution (4)+225 µl of water) and the tube is gently inverted. After, then 270 µl of solution (5) is added and the tube is gently inverted (color change from brown→clear).

C. Preparation of the Gold Nanorods

To prepare the gold nanorods, 80 µl of gold seed solution is added to the growth solution, above. The solution is mixed gently for 10 seconds. The solution is left to sit for 6 hours without any intervention. If the seed solution seems to have crystallized due to the CTAB, the solution is reheated in a water bath, e.g., at setting "3", until the CTAB re-dissolves.

D. Obtaining Pure Nanorods and Removing CTAB

The nanorods are left undisturbed for at least 24 hours for the nanorods to sediment to the bottom of the test tube. The bottom portion of the nanorod sample will typically contain the least amount of gold spheres/chunks.

CTAB may be removed by heating (in the hot water bath) the nanorod sample to re-dissolve the CTAB, and then quickly centrifuged at 8500 rpm for 20 minutes. The supernatant is removed and pellet re-dispersed with water. The process is repeated once more and the pellet re-dispersed in $DDH_2O$. The concentration of the nanorods can be controlled at this step.

1. Preparation of Nanorods Exhibiting Plasmon Resonance at 980 nm

The following protocol can be used to prepare gold nanorods exhibiting plasmon resonance at 980 nm. The reagents and amounts used to prepare the solutions need for nanorod synthesis are shown below: 1.641 CTAB: in a 50 mL centrifuge tube; 1.782 g BDAC (benzyldimethylhexadodecylammonium chloride, FW 396.09) in a 50 mL centrifuge tube; 0.023 g $NaBH_4$ in a glass vial; 0.017 g $AgNO_3$ in a glass vial; 0.0352 g ascorbic acid (AA) in a glass vial.

The following solutions are prepared:

1. CTAB Solution:

To prepare the CTAB solution, water is heated in a 500 mL beaker (e.g., set the hot plate setting to "3"). To the CTAB containing tube, 15 mL of DI water is added and the tube is immersed in the heated water. Sonication is occasionally applied and gentle shaking to dissolve the CTAB completely.

2. BDAC Solution:

To prepare the BDAC solution, 15 mL of water is added to the tube containing BDAC and is immersed in heated water. Sonication is occasionally applied and the tube gentle shaken to dissolve the BDAC completely.

3. Au Solution:

To prepare the Au solution, 27 mL of DI water was added to a 50 mL centrifuge tube with 1.125 mL of Au (a 0.025 M stock solution). Iced water in a centrifuge tube was taken out of the freezer.

Preparation of the Seed Solution:

To prepare the seed solution, 1.5 mL DI water was added to 3 mL of the CTAB solution in a 15 mL centrifuge tube (see Solution-1). To this solution was added 1.5 mL of the Au solution (see Solution-3), followed by gently shaking the tube to mix the solution.

To a glass vial containing 0.023 g of $NaBH_4$, 600 μL of ice cold water was added. The $NaBH_4$ is dissolved quickly using a pipet. 6 μL of this $NaBH_4$ solution is added to 594 microliters of ice cold water in a 2 mL centrifuge tube. 200 μL of this diluted $NaBH_4$ solution was combined with 160 μL of the CTAB/Au solution in a 15 mL centrifuge tube, followed by gently shaking the tube to mix the solution for about 2 min. The solution is left to stand, and this seed solution should be used in 2 hours.

Preparation of the Growth Solution:

To prepare the growth solution, 15 mL of BDAC solution (solution-2) was added to a 50 mL tube, followed by addition of 10 mL of CTAB solution (solution-1), followed by gentle shaking to mix the surfactant. To this solution was added 25 mL of Au solution (solution-3), followed by gently shaking to mix the solution.

An $AgNO_3$ solution was prepared as follows. 1 mL of DI water was added to 0.017 g of $AgNO_3$ in a vial, followed by shaking well to completely dissolve the reagent. 960 μL of DI water was added to a 2 mL centrifuge tube. 40 μL of the $AgNO_3$ solution above was added to the 2 mL centrifuge tube, followed by mixing. 900 μL of the diluted $AgNO_3$ was added to the BDAC/CTAB/Au solution above in a 50 mL tube, and was mixed well by shaking. An ascorbic acid solution was prepared as follows: 0.0352 g of ascorbic acid was added to 2 mL of DI water, followed by shaking well to dissolve the ascorbic acid completely. 300 μL of this solution was transferred to the 50 mL tube containing CTAB/BDAC/Au, followed by shaking gently to mix the solutions. To this solution was added 50 μL of seed solution, prepared above, followed by gentle shaking to mix the solutions, and incubated still overnight at 35° C.

Figure 2:
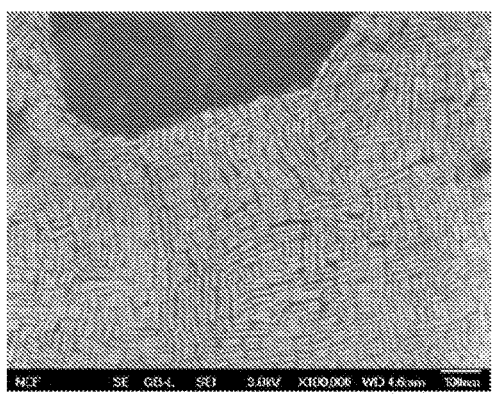
FIG. 2. (a) Scanning electron micrograph (SEM) and (b) optical extinction spectrum of gold nanorods synthesized by the wet chemistry method.
Figure 2:
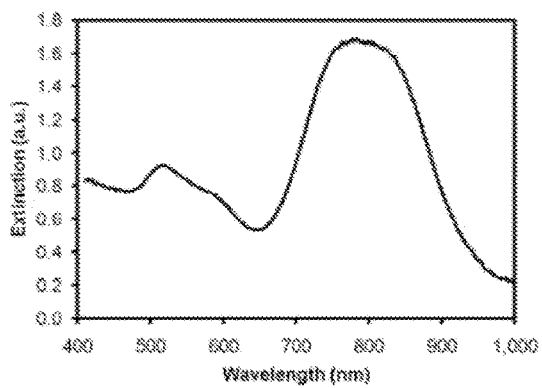

The rod length of the nanorods is controlled by the concentration of gold ions in the growth solution and also by the composition of various materials also added in the growth solution, which can include silver nitrate ($AgNO_3$) and ascorbic acid. Gold nanorods prepared according to these general methods are shown in FIG. 2(*a*). It is evident that highly uniform nanorods are obtained by this method. The experimentally measured extinction spectrum is shown in FIG. 2(*b*). It shows two distinct peaks at 520 and 800 nm which correspond to the traverse and longitudinal plasmon, respectively. There was also a small shoulder at 600 nm, which is attributed to the small fraction of spherical particles unintentionally produced in the solution. These particles can be removed by a purification process, but it is not critical if a small number of nanoparticles of this size remain, because the treatment procedure uses targeted heating at a higher wavelength and thus the smaller wavelength peaks will not significantly contribute. Khanal et al. *J Am Chem Soc* 130(38):12634-5 (2008).

Example 2

Conjugation of Gold Nanorods to Antibody

The nanorods were conjugated with anti-EGFR antibody (Erbitux 08000212B 2 mg/ml) by using a two-step protocol reported similar to established methods of others. Patra et al. *Cancer Res* 68(6):1970-8 (2008). In the first step, the gold nanorods were centrifuged into a pellet and washed twice with 1 ml milliQ water, before being incubated with 1 ml (PEG) OPS-SPEG-SVA (1 mM, 1 mL, Laysan Bio, MW: 5000) at room temperature overnight with gentle rocking (20 rpm). Excess OPSS-PEG-SVA was removed from the nanorods by centrifugation and pellet formation and washed twice with 1 ml DPBS-0.05% Tween-20. In the second step, the PEGylated gold nanorods were incubated with 0.5 ml of the EGFR-directed antibody C-225 (Erbitux 2 mg/ml). The sample was then centrifuged for 10 minutes at 12,000 rpm to remove excess antibodies and washed twice with 1 ml DPBS-0.05% Tween-20 before being resuspended in 1 ml blocking solution (0.5% BSA-DPBS-0.05% Tween-20). The conjugated nanorods were then stored in dark at 4° C.

Example 3

In Vitro Binding of Gold Nano-EGFR to Human Bladder Cancer Cells

Figure 3:
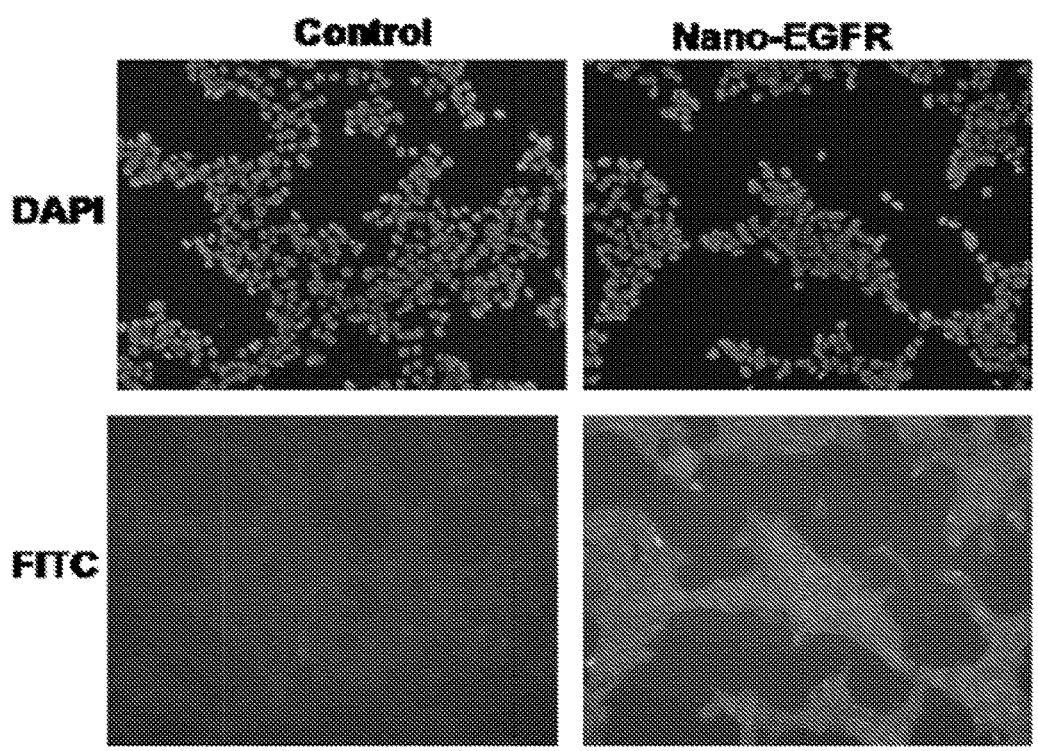
FIG. 3. Live cells binding assay. Primary bladder cancer cell line 2008B17 was seeded on 8-well chamber slide, 0.5 ml/well. Gold Nano-EGFR or control was added before the cells were fixed in formalin. In the control experiment, the naked gold nanorods do not associate with the cancer cells. DAPI demonstrated cellular arrangement with the FITC demonstrating the gold nanorod.

Once the gold nano-EGFR was available, we tested its binding with human bladder cancer cells in vitro. HTB9 (American Type Culture Collection, Manassas, Va., USA) and primary bladder cultures were grown in OptiMEM (Gibco, Grand Island, N.Y., USA) with 3.75% fetal bovine serum (Gemini, Woodland, Calif., USA) and 100 units streptomycin-penicillin sulphate (Life Technologies, Grand Island, N.Y., USA). All cell lines were incubated at 37° C.

with 5% $CO_2$. The cells were trypsinized to detach from the flask and neutralized with fetal calf serum (FCS) containing medium. The cells were collected by centrifugation and the supernatant aspirated, before being washed twice with DPBS. The cell pellet was then resuspended in 5 ml 2% formaldehyde and incubated at 37° C. for 10 minutes to fix the cells. Centrifugation was used to collect the cells and they were incubated with 90% methanol in ice for 30 minutes causing permeabilization. The cells were then washed twice with incubation buffer (0.5% BSA-DPBS) before being resuspended in the blocking buffer with $5 \times 10^6$ cells/ml. The cells were blocked in incubation buffer for 30 minutes at room temperature, followed by incubation with 1) nano-EGFR, 2) naked nanorods. Dylight™ fluorescent dye-conjugated secondary antibody goat anti-human IgG (Jackson lab) was used for detection. The binding of the gold nanorods and the C-225 antibody (humanized mouse antibody against EGFR) was detected by fluorescent microscopy (FIG. 3). In this figure, DAPI (blue color) stains the nucleus of bladder cancer cells indicating the presence and arrangement of cells in the slides. FITC (green color) indicates the distribution of the nano-EGFR binding, which strongly correlates with the cellular distribution. Taken together, these data demonstrate the in vitro binding of gold nanorod-C225 conjugate (nano-EGFR) to bladder cancer cells.

Example 4

Photothermal Ablation Using the Nanorods Coupled to EGFR Antibody

Figure 4:
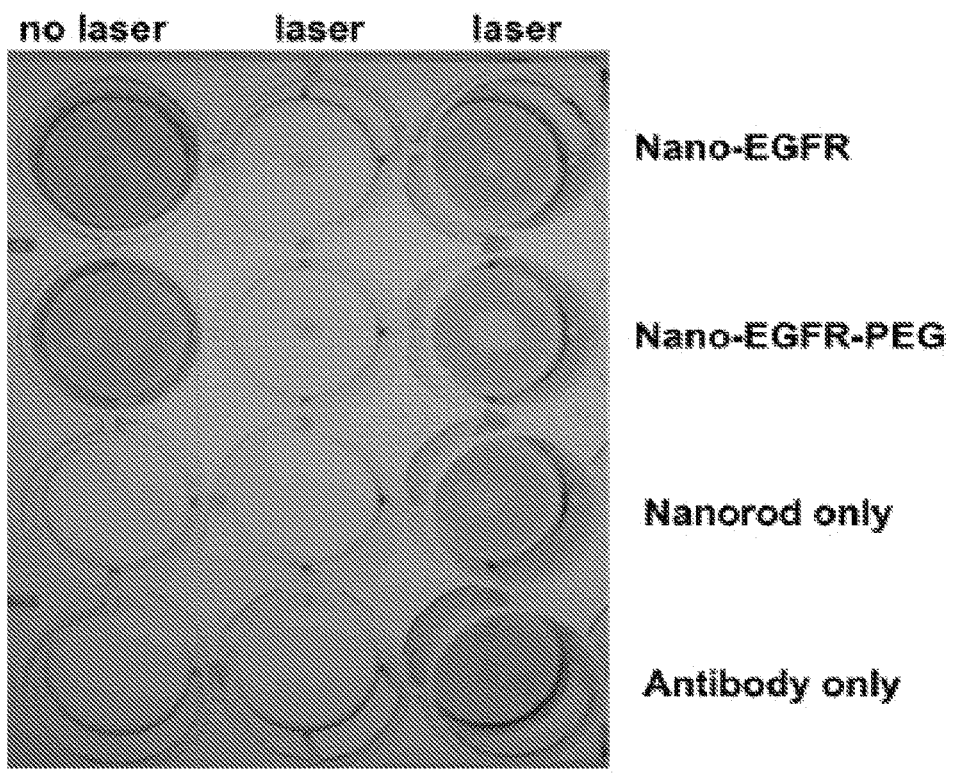
FIG. 4. Demonstration of cellular killing. HTB9 cells were plated and exposed to nano-EGFR or controls for 2 hours. Laser treatments were given at 750 nm (380 mW) for 5 minutes. Note that the laser treatment area corresponds to a small 2 $mm^2$ zone in the middle of the well. Columns 1 and 3 show neutral red staining and column 2 shows trypan 2 staining.

With clear evidence of in vitro binding, we next investigated the killing specificity of nano-EGFR in human bladder cancer cells treated with laser-generated near infrared light. HTB-9 cells were seeded in 24-well plates and treated with nano-EGFR (or controls) for two hours. This treatment time was selected to mimic the longest intravesical treatment that is tolerated in humans. The treatment media was then removed; the cells were washed once with 1 ml medium, before 100 µl of fresh media was added back prior to the laser treatment, with an additional 0.5 ml of media added immediately after the laser treatment. The laser treatments were given at a wavelength of 750 nm, power at 380 mW, area approximately 2 $mm^2$ for 5 minutes. Cells were placed back in the $CO_2$ incubator for 3 hours, before being stained with neutral red or trypan blue. FIG. 4 demonstrates the specific and robust ablation of bladder cancer cells treated with both nano-EGFR and laser therapy. In the middle column, both nano-EGFR and nano-EGFR PEG yield trypan blue staining precisely in the area of the NIR energy while this is not seen in the control conditions of gold nanorods or EGFR antibody alone, indicating the specificity of cell killing based on the presence of Nano-EGFR, with improved effectiveness using the PEG formulation. The Right column confirms the loss of viable cells in this same region via neutral red staining, with greater killing suggested with the PEG form.

Example 5

Demonstration of Multifunctionality of the Nanomaterials In Vitro in Human Bladder Cancer Cells The functionalities of the multifunctional nanomaterials are tested in vitro. Human bladder cancer cells HTB9 are plated ($5 \times 10^4$ cells/well) in a 96 well plate. When the cells reach confluence (approximately 24 hours later), they are exposed to a range of specific concentrations of multifunctional nanomaterials (in triplet). The LiCor two laser imaging system is utilized to detect the binding of the nanomaterials to cells. To demonstrate fluorescence imaging, the cells are illuminated with low intensity 980 nm laser light and the visible fluorescence is imaged using a standard optical microscope. For thermal ablation, the experimental conditions will be similar to those used to demonstrate thermal ablation using nano-EGFR as described above.

Example 6

Demonstration of Multifunctionality of the Nanomaterials In Vivo Using an Orthotopic Bladder Cancer Model Bladder cancer cells with transfected luciferase will be implanted into female athymic nude mice. Since the efficacy of xenograft implantation is approximately 75%, each mouse will undergo luminescent imaging at day 7 to sort out the minority of mice without successful tumor cell implantation on the basis of their lack of luciferase activity. Three days post luminescent imaging, the multifunctional nanoparticles will be instilled at various concentrations intravesically into the mice with successful implantation. We expect the multifunctional nanoparticles will quickly associate with the bladder tumors in our model since they will be in immediate contact with the cells after administration, as opposed to the delayed exposure observed with systemic delivery methods. The mice will then be subject to near infrared laser illumination with a range of light doses. Since infrared light is able to safely penetrate several cm into viable tissue, we will study the efficacy of externally delivered infrared light. The effect of the laser treatment will be monitored by the luciferase images. We will also sacrifice a small number of mice after the multifunctional nanoparticle instillation, exposing the bladder and allowing for in situ confirmation of the binding and fluorescent capacity of the multifunctional nanoparticle in the animal model.

Example 7

Conjugation of Gold Nanorods and Up-Conversion Phosphors

Before the up-conversion phosphor is conjugated to the gold nanorod, it is first processed to make it more water soluble by removing surface oleic acid present on the upconversion phosphor. About 30 mg of $NaYF_4:Yb^{3+},Er^{3+}$ UCP is added to a glass vial and 3 mL of HCl (pH 3.5) was added to it, followed by stirring for at least 2 hours, typically overnight. 1 mL of ether is added while stirring. The ether phase is moved to another glass vial. Another 1 mL of ether is added to the glass vial, followed by stirring and removing the ether phase to the ether containing glass vial. Another 1 mL of ether is added to the glass vial, followed by stirring and removing the ether phase to the ether containing glass vial. 1 mL of water was added to the glass vial containing the ether extract and the vial was shaken. The water phase was moved to the original vial containing the UCP. Acetone was added to precipitate the upconversion phosphor followed by centrifugation (1500 rpm×20 min). The supernatant is removed and 4 mL of acetone is added, followed by centrifugation at 2000 g for 4 minutes. The supernatant is removed and mixed with 20 mL of isopropyl alcohol.

Aminopyrene-1,3,6-trisulfonate (APTS) Treatment

The upconversion phosphor is then treated with APTS. 120 uL of APTS is added to the above UCP in isopropyl alcohol, followed by stirring at 85° C. for 24 hours, then centrifugation at 1500 rpm×20 min. It is then washed with ethanol 5×. After centrifugation, the supernatant is removed and 1 mL of DMF is added. 50 mg of OPSS-PEG-SVA is measured in 500 uL DMF. 500 uL APTS treated UCP is mixed with 500 uL PEG and stirred for 20 hours, followed by centrifugation and washing with water 5×.

The processed upconversion phosphor was then conjugated to the gold nanorods (100 nm length) at various ratios, by combining the upconversion phosphor and gold nanorods in water and mixing.

Example 8

Figure 6:
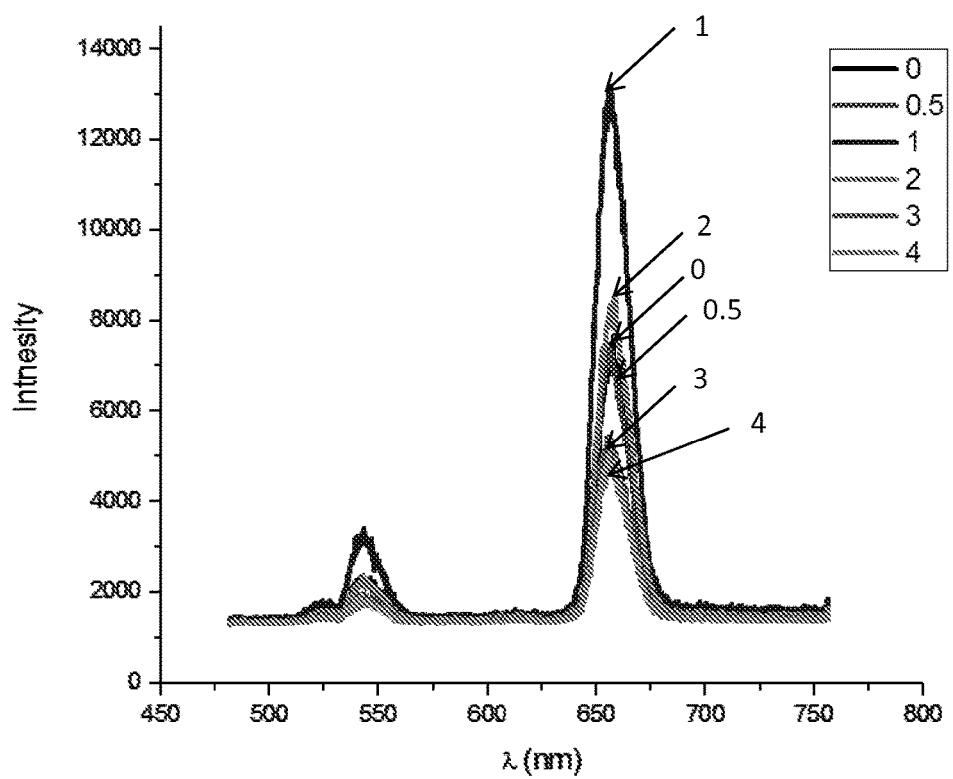
FIG. 6. Upconverted luminescence intensity of an upconversion phosphor—gold nanorod complex. The numbers in the legend (0-4) indicate the amount of nanorod relative to the amount of upconversion phosphor present. The luminescence intensity of the upconversion phosphor is enhanced when conjugated to a specified quantity of gold nanorods.

Upconverted Luminescence Intensity of the Upconversion Phosphor-Gold Nanorod Complex To determine if the surface plasmon resonance absorption of the gold nanorod can enhance the efficiency of frequency up-conversion of the up-conversion phosphor, the luminescence intensity of the upconversion phosphor was investigated in the context of the upconversion phosphor-gold nanorod conjugate. The amount of gold nanorod present varied from a ratio of 0 nanorods per upconversion phosphor (no complexes) to 4 nanorods/upconversion phosphor. See FIG. 6. The complexes were subjected to near infrared light at 980 nm, and the visible luminescence was measured at about 655 nm. An enhancement in the intensity of frequency up-conversion was observed at certain ratios of nanorods to upconversion phosphors while at other ratios, a reduction was observed. FIG. 6. Nanorods can block the incident light and can quench some luminescence as well as provide enhancement, so there is an optimum ratio between the upconversion phosphor and the nanorod. These data support that surface plasmon resonance absorption of the gold nanorod can enhance the efficiency of frequency up-conversion of the up-conversion phosphor. As a result of the increased intensity and enhanced frequency upconversion, significantly improved visualization and imaging of the complex can be achieved, to aid in the detection and killing of cancer cells in vivo.

Example 9

Plasmon Enhanced Fluorescence Up-Conversion

In this example, three sets of data are presented. First, we developed a new coating technique for upconversion phosphor (UCP) which makes them water-soluble and also negatively charged. The negative surface charge on the UCP surface alleviates the agglomeration problem by electrostatic repulsion between UCP and also allows us to use charged polyelectrolyte molecules to deposit highly uniform films of UCP nanoparticles in a layer-by-layer fashion.

Next, to demonstrate the mechanism of enhanced up-conversion and yet achieve better control of coupling between gold nanorod (GNR) and up-conversion phosphor (UCP), we conducted two different series of experiments: (1) layer-by-layer deposition of UCP and GNR with precisely defined separations using polyelectrolytes and (2) layer-by-layer deposition of UCP on metallic nanograting structures with dimensions similar to GNRs.

1. Preparation of Water-Soluble UCP by PMAO Coating

Figure 7:
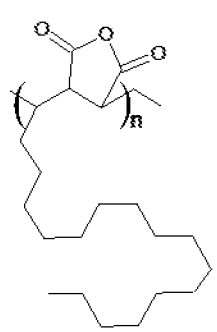
FIG. 7 (A) PMAO molecular structure and the introduction of amine terminated functional group (B) schematic of PMAO-methoxyethyleamine coated UCP and (C) schematic of PMAO-PEG coated UCP. In both cases, the PMAO backbone presents negatively charged surface.
Figure 7:
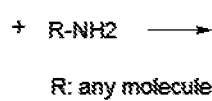
Figure 7:
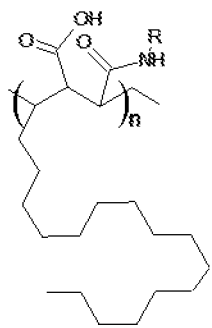
Figure 7:
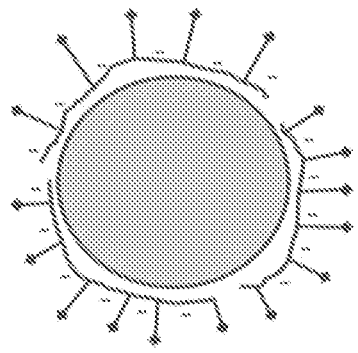
Figure 7:
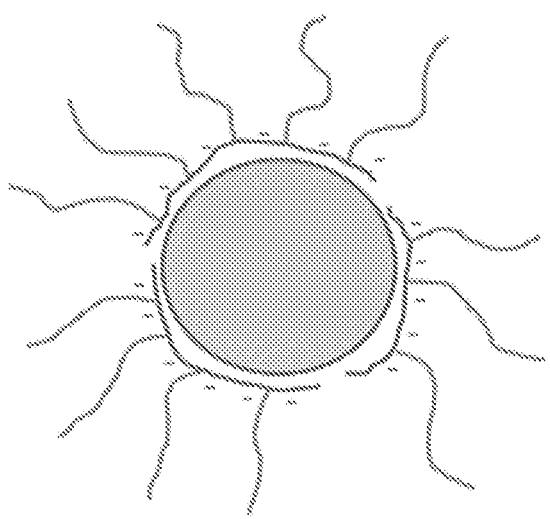

Poly(maleic anhydride-alt-octadecene) (PMAO) is a water insoluble polymer but the maleic anhydride backbone allows amine-derivatized molecule to be grafted. If water-soluble molecule is grafted through this process, the polymer turns amphiphilic and can therefore be used to coat the surface of water-insoluble nanoparticle to make them water soluble. This has been used to turn water-insoluble CdSe quantum dot (QD) water-soluble (J. Yang, S. R. Dave, and X. Gao, "Quantum Dot Nanobarcodes: Epitaxial Assembly of Nanoparticle—Polymer Complexes in Homogeneous Solution," J. Am. Chem. Soc. 130, 5286-5292 (2008)). We have successfully applied this technique to UCP for the first time. We developed two procedures for PMAO coating. In both cases, the coating of PMAO remains the same but the grafting of amine-derivatised molecules are different. In the first method, we graft methoxyethylamine ($CH_3OCH_2CH_2$—$NH_2$). This is a small molecule and thus the coated particle size remains largely unchanged. We found the UCP nanoparticles tend to agglomerate at low pH values and thus the coating procedure has to be carried out at close to neutral pH values. The second method is to graft poly(ethylene glycol) (PEG) onto the backbone of PMAO. PEG grafted PMAO-UCP particles were more stable against pH variations. PEG also has many advantageous features for biological applications such as biocompatibility and long circulation time. PEG is a larger molecule than methoxyethyleamine so the hydrodynamic radius of coated UCP particle tends to become larger. The main result, however, in both cases was that the PMAO-coated UCP nanoparticles were well-dispersed in water, which make the particles applicable to many biological applications. See FIG. 7.

2. Layer-by-Layer (LbL) Deposition of PMAO-Coated UCP

Figure 8A:
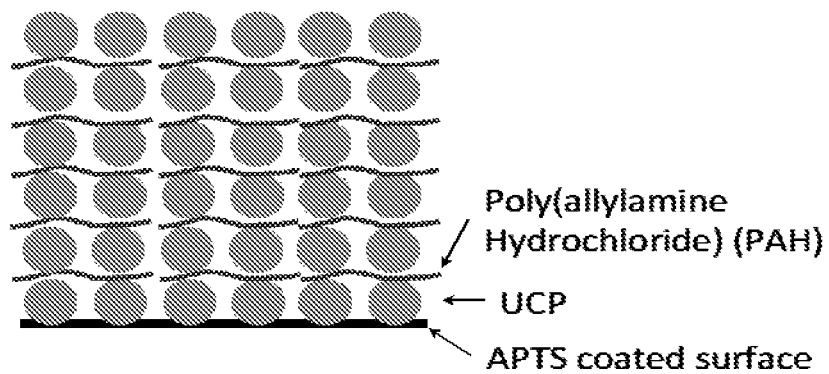
FIG. 8 (A) Schematic of layer-by-layer deposition of UCP using PAH as electrostatic intervening layer (B) Thickness of UCP layers measured by AFM (C) upconverted luminescence intensity (540 nm green and 650 nm red peak intensities) as a function of number of UCP layers.
Figure 8B:
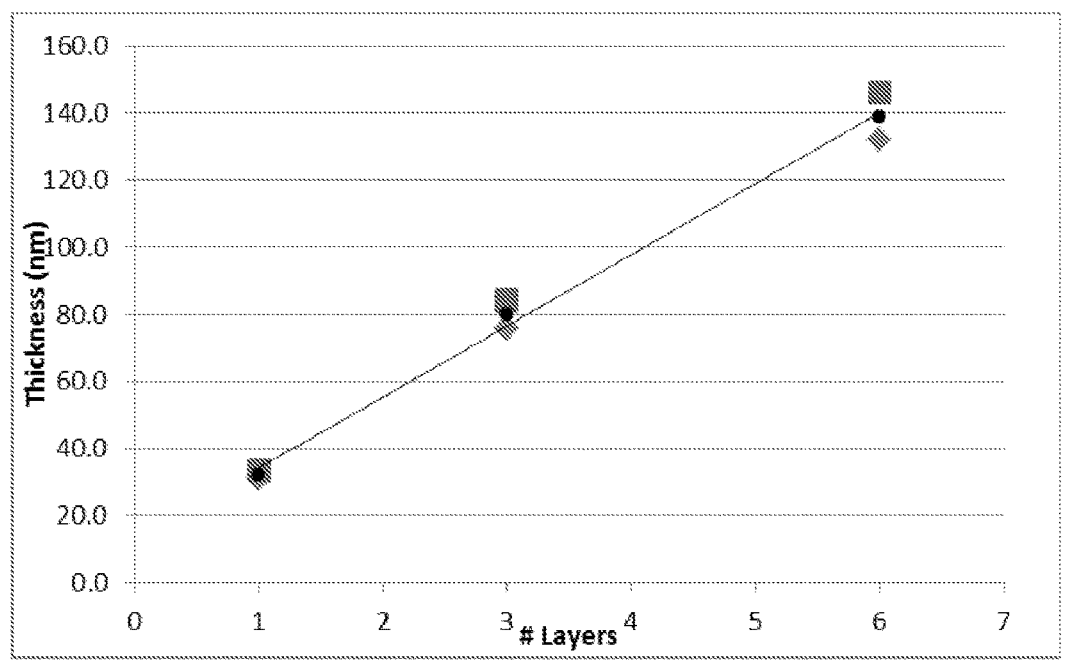
Figure 8C:
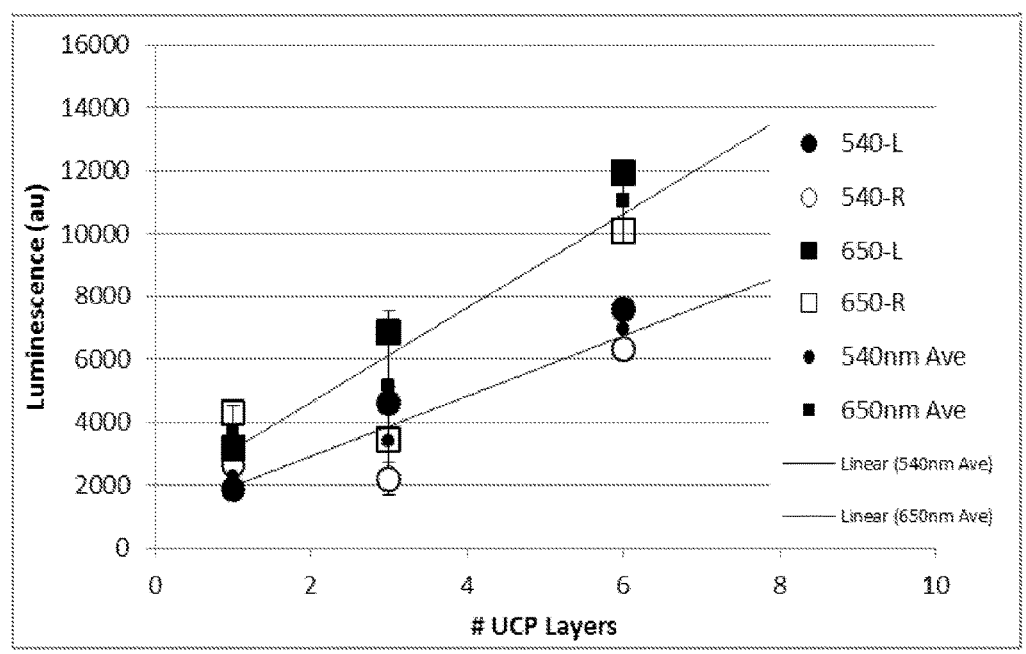

Taking advantage of the fact that the PMAO-coated UCP is well dispersed in water and also is negatively charged, we conducted layer-by-layer deposition of UCP mediated by electrostatic interaction. For this, we first prepared positively charged substrate surface by coating 3-aminopropyltriethoxysilane (APTS) on glass or silicon substrate. First layer of UCP is then directly applied to the APTS-coated surface by drop-casting. The electrostatic attractive interaction between the positively charged substrate surface and the negatively charged UCP surface induces strong binding between the two, forming a layer of UCP particles on the substrate surface. Furthermore, the electrostatic repulsion among the UCP particles prevents any aggregation of UCP particles and we obtain highly uniform monolayer of UCP particles. For subsequent deposition of additional UCP layers, we first coat the UCP layer with poly(allylamine hydrochloride) (PAH), a positively charged polymer, by drop-casting followed by the next layer of UCP deposition by drop-casting. This procedure can be repeated to obtain the desired thickness of UCP film, as schematically shown in FIG. 8A. To confirm successful layer-by-layer deposition, we conducted thickness measurements by atomic force microscopy (AFM) and upconverted luminescence intensity measurements by photoluminescence (PL) spectroscopy where we used 980 nm laser excitation and monitored the upconverted luminescence peaks at 540 nm and 650 nm. The results are shown in FIGS. 8B and C and the linear relationship between the number of layers and thickness/luminescence clearly indicate the layer-by-layer nature of deposition. From the slope of the AFM thickness data, the thickness of a single UCP+PAH layer was estimated to be 22 nm, which was in excellent agreement with the UCP particle size measured by transmission electron microscopy (TEM).

3. Coupling of GNR and UCP by LbL Co-Deposition

Figure 9:
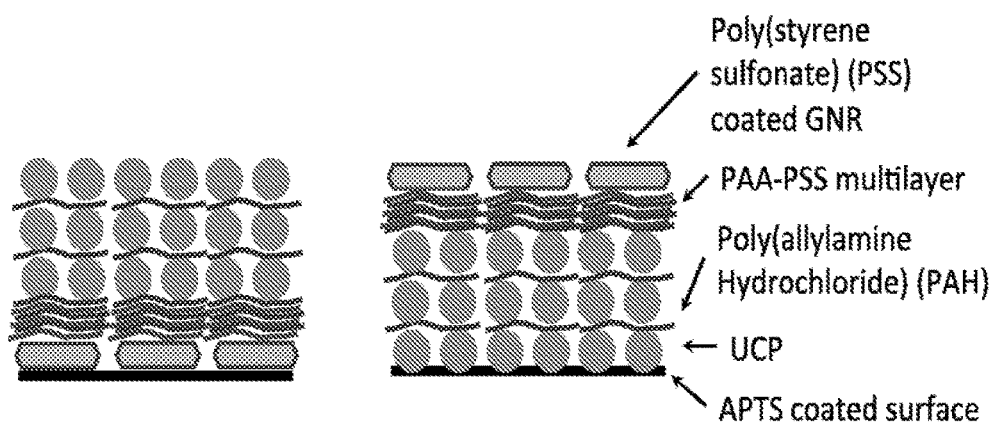
FIG. 9. Schematic diagrams of LbL deposited UCP and GNR.

We then proceeded to deposit UCP together with GNR to show the coupling between the two. Two different configurations were prepared—GNR on top of or underneath the UCP multilayer. Also, in order to precisely control the separation distance between GNR and UCP, which is critical to maximize the enhancement effect, we prepared a spacer layer composed of multilayers of PAH and poly(styerene sulfonate) (PSS). PSS is a polymer with negative charge and thus efficiently form a monolayer on positively charged surface such as PAH layer. Also, the GNR was coated with PSS so that it could efficiently form a monolayer on top of PAH coated surface. The multilayer structures of GNR and UCP are schematically shown in FIG. 9.

Figure 10:
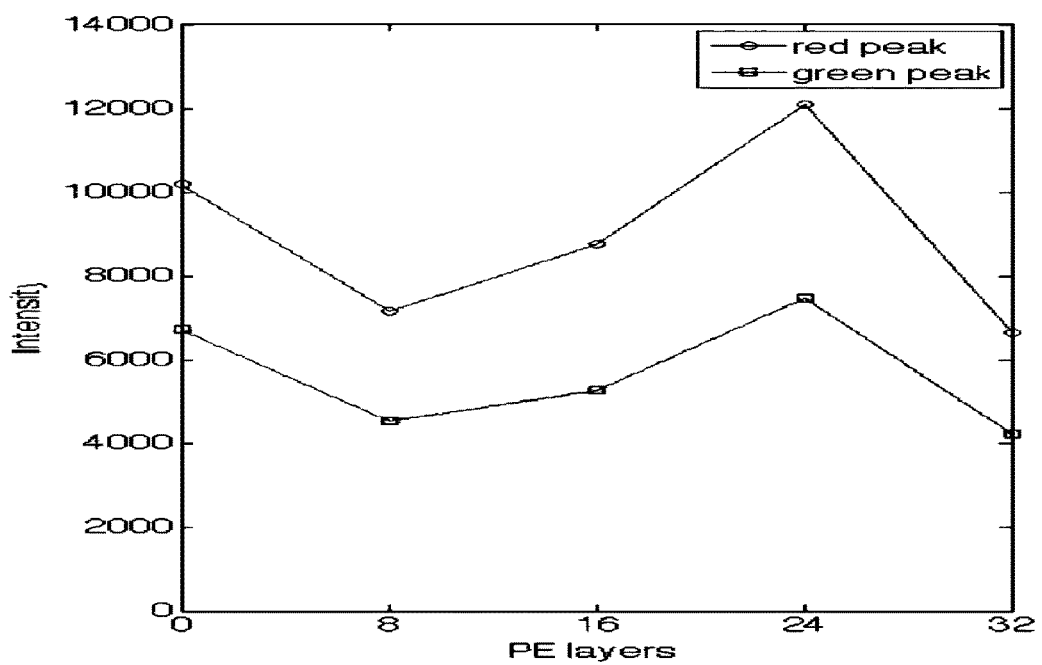
FIG. 10. PL intensity as a function of the spacer (PAH-PSS) layer thickness. The x-axis shows the number of polymer layers each of which is ~1.0 nm thick. 24 layer thick spacer showed enhancement of about 20%.

The PAH-PSS multilayer thickness can be precisely controlled by the number of polymer layers. A single polymer layer was 0.7~1.0 nm thick, according to the AFM thickness measurements. After preparing a series of samples containing 3 layers of UCP and monolayer of GNR separated by various thickness of PAH-PSS multilayer, we conducted the PL spectroscopy. As shown in FIG. 10, we observed enhanced upconverted luminescence for 24 layers of PAH-PSS. The enhancement was about 20% for the red emission. While this could be further enhanced when the sample geometry and preparation conditions are fully optimized, this result clearly shows that the enhanced upconverted luminescence is achievable by coupling GNR with UCP.

Figure 11A:
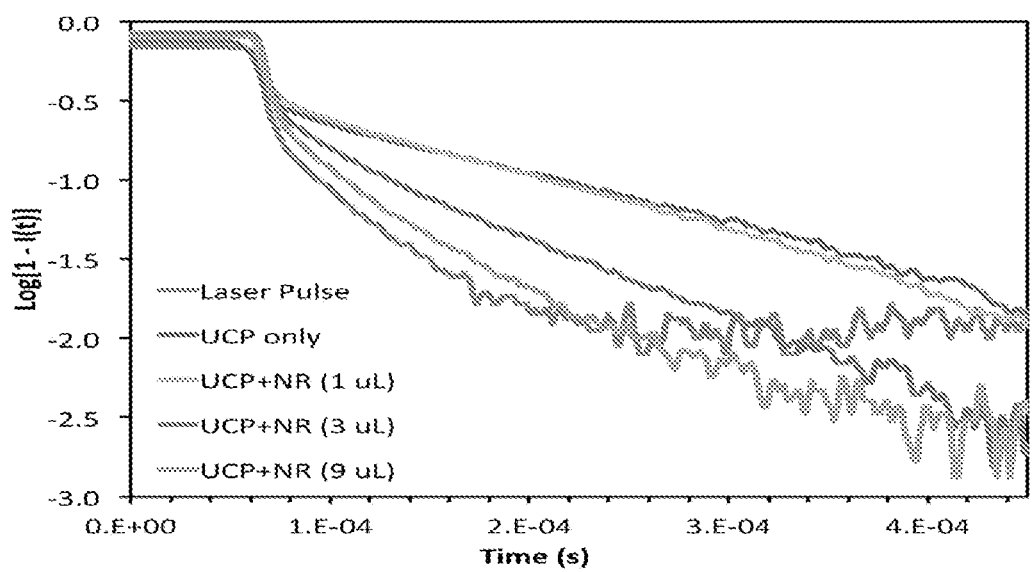
FIG. 11. (A) Rise and (B) decay of the upconverted luminescence from UCP as a function of the amount of GNR added to the sample.
Figure 11B:
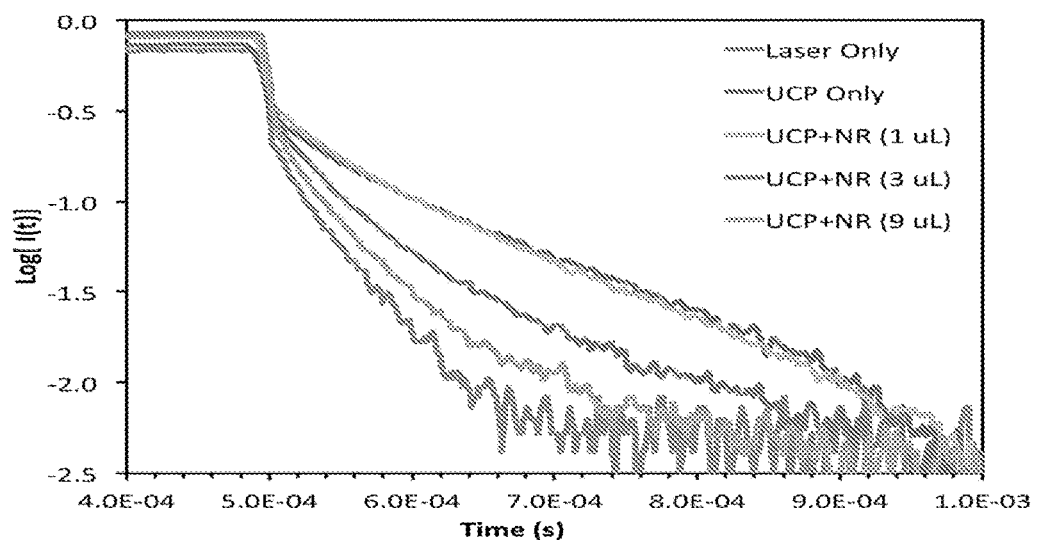

We further conducted time-resolved spectroscopy to directly probe the upconversion process. GNR is expected to influence the upconversion process in two ways—enhance the upconversion by accelerating the energy transfer process and quench the luminescence by providing nonradiative decay path. The former should manifest itself as shortened rise time while the latter will cause shorted decay time of the upconverted luminescence. In these experiments, the UCP-GNR samples were excited by a square pulse of 980 nm laser and the rise and decay of the upconverted luminescence was recorded as a function of time. FIG. 11A shows the rise of the luminescence plotted in semilog scale. Note that we plotted $\log(1-I(t))$ so that the decreasing curve actually represents a rising curve. It is clearly shown that the rise time was shortened and the luminescence rises faster when GNR is added. This is a direct evidence of enhanced energy transfer process which promotes quicker excitation into the upconversion state. FIG. 11B, on the other hand, shows the luminescence decay in semilog scale. Here also the decay becomes faster as GNR is added, indicating the onset of quenching. These two opposite effects are in competition, resulting in decrease or increase of the total upconverted luminescence intensity. Optimization of the sample preparation techniques should therefore seek for the condition where the quenching is minimized while the enhancement is maximized. In any case, these results clearly show that the surface plasmon supported by GNR enhances the upconversion process.

While there have been shown and described what are presently believed to be the preferred embodiments of the present invention, those skilled in the art will realize that other and further embodiments can be made without departing from the spirit and scope of the invention described in this application, and this application includes all such modifications that are within the intended scope of the claims set forth herein.

What is claimed is:
1. A multifunctional nanomaterial comprising
   i) a nanorod comprising a noble metal, wherein the nanorod exhibits surface plasmon resonance absorption in the near-infrared spectrum;
   ii) an up-conversion phosphor that absorbs infrared light and emits visible luminescence; and
   iii) a biomolecule targeting moiety,
wherein the biomolecule targeting moiety is an antibody that specifically binds epidermal growth factor receptor expressed on the surface of a bladder cancer cell, a skin cancer cell, or an oral cancer cell, wherein the up-conversion phosphor is indirectly conjugated to the nanorod via a linker, wherein the surface plasmon resonance of the noble metal nanorod enhances the efficiency of frequency up-conversion of the up-conversion phosphor, and wherein the multifunctional nanomaterial is capable of emitting visible luminescence and increasing in temperature when exposed to one or more intensities of infrared light.

2. The multifunctional nanomaterial of claim 1, wherein the nanorod is a gold nanorod.

3. The multifunctional nanomaterial of claim 2, wherein the nanorod has an aspect ratio of from about 3.5 to about 6.5.

4. The multifunctional nanomaterial of claim 1, wherein the surface plasmon resonance absorption maximum is from about 800 nm to about 1300 nm.

5. The multifunctional nanomaterial of claim 1, wherein the up-conversion phosphor comprises optically active donor and acceptor ions embedded in a host material.

6. The multifunctional nanomaterial of claim 5, wherein the donor and acceptor ions are rare earth ions.

7. The multifunctional nanomaterial of claim 6, wherein the rare earth ions are selected from the group consisting of $Yb^{3+}$, $Er^{3+}$, $Eu^{3+}$, $Tb^{3+}$, $Ce^{3+}$, $Pr^{3+}$, $Nd^{3+}$, $Gd^{3+}$, $Sm^{3+}$, $Dy^{3+}$, $Ho^{3+}$ and $Tm^{3+}$.

8. The multifunctional nanomaterial of claim 7, wherein the host material is selected from the group consisting of $YF_3$, $NaYF_4$, $ZrF_4$, $AlF_3$, $BaY_2F_8$, $BaCl_2$, $YOCl$, and $Y_2O_3$.

9. The multifunctional nanomaterial of claim 8, wherein the up-conversion phosphor is selected from the group consisting of $NaYF_4:Yb^{3+},Er^{3+}$, $SrF_2:Er^{3+}$, $YF_3:Yb^{3+},Tb^{3+}$, $YbPO_4:Yb^{3+}$, $CaF_2:Eu^{2+}$, $YF_3:Yb^{3+},Tm^{3+}$, $NaYF_4:Yb^{3+},Tm^{3+}$, $Na_2Y_3F_{11}:Yb^{3+},Er^{3+}$, $YF_3:Yb^{3+},Er^{3+}$, $SrCl_2:Yb^{3+}$ and $SrCl_2:Yb^{3+},Tb^{3+}$.

10. The multifunctional nanomaterial of claim 9, wherein the up-conversion phosphor absorbs infrared light with a wavelength of from about 800 nm to about 1100 nm.

11. The multifunctional nanomaterial of claim 1, wherein the biomolecule targeting moiety comprises a monoclonal antibody.

12. The multifunctional nanomaterial of claim 1, wherein the linker comprises PEG.

* * * * *